United States Patent
Whiting et al.

(10) Patent No.: US 12,344,587 B2
(45) Date of Patent: Jul. 1, 2025

(54) SYNTHETIC RETINOIDS FOR USE IN RAR ACTIVATION

(71) Applicant: UNIVERSITY OF DURHAM, Durham (GB)

(72) Inventors: Andrew Whiting, Durham (GB); David Chisholm, Durham (GB); Iain Greig, Aberdeenshire (GB); Thabat Khatib, Aberdeenshire (GB); Peter McCaffery, Aberdeenshire (GB)

(73) Assignee: UNIVERSITY OF DURHAM (GB)

( * ) Notice: Subject to any disclaimer, the term of this patent is extended or adjusted under 35 U.S.C. 154(b) by 885 days.

(21) Appl. No.: 17/435,939

(22) PCT Filed: Mar. 11, 2020

(86) PCT No.: PCT/GB2020/050607
§ 371 (c)(1),
(2) Date: Sep. 2, 2021

(87) PCT Pub. No.: WO2020/183173
PCT Pub. Date: Sep. 17, 2020

(65) Prior Publication Data
US 2022/0144783 A1     May 12, 2022

(30) Foreign Application Priority Data
Mar. 11, 2019   (GB) ................................. 1903242

(51) Int. Cl.
*C07D 241/38*  (2006.01)
*A61P 25/28*  (2006.01)
(Continued)

(52) U.S. Cl.
CPC ............ *C07D 241/38* (2013.01); *A61P 25/28* (2018.01); *C07C 63/74* (2013.01); *C07C 65/26* (2013.01);
(Continued)

(58) Field of Classification Search
CPC .. C07D 241/38; C07D 213/79; C07D 213/80; C07D 233/96; C07D 241/24;
(Continued)

(56) References Cited

U.S. PATENT DOCUMENTS 5,149,705 A     9/1992  Chandraratna
5,149,707 A *   9/1992  Bartroli ................ C07D 233/56
                                                          514/396

FOREIGN PATENT DOCUMENTS

EP       0284261 A1    9/1988
EP       3428155 A1    1/2019
(Continued)

OTHER PUBLICATIONS

Gambone, Carlo J., et al. "Unique property of some synthetic retinoids: activation of the aryl hydrocarbon receptor pathway." Molecular pharmacology 61.2 (2002): 334-342. (Year: 2002).*
(Continued)

*Primary Examiner* — Clinton A Brooks
*Assistant Examiner* — Izabela Schmidt
(74) *Attorney, Agent, or Firm* — K&L GATES LLP

(57) ABSTRACT

The present invention relates to compounds of formula I: in which $A^1$-$A^7$ and $R^1$ to $R^5$ are defined herein, for use in the treatment of a condition or disease which is alleviated by the activation of retinoic acid receptors (RAR). The invention also relates to pharmaceutical compounds comprising such compounds, and related methods of treatment. In an aspect, the invention relates to a method of screening compounds for therapeutic potential in the treatment of a condition or disease which is alleviated by the activation of retinoic acid receptors (RAR). Aspects of the invention relate to novel compounds of formula I in which at least one of $A^1$ to $A^3$ is N or at least one of $A^4$ is $CR^{12}$ or $A^5$ is $CR^{13}$ in which $R^{12}/R^{13}$ is halogen.

14 Claims, 11 Drawing Sheets

(51) Int. Cl.

| | |
|---|---|
| *C07C 63/74* | (2006.01) |
| *C07C 65/26* | (2006.01) |
| *C07D 213/79* | (2006.01) |
| *C07D 213/80* | (2006.01) |
| *C07D 233/96* | (2006.01) |
| *C07D 241/24* | (2006.01) |
| *C07D 401/06* | (2006.01) |
| *C12Q 1/48* | (2006.01) |
| *G01N 33/50* | (2006.01) |
| *G01N 33/68* | (2006.01) |

(52) U.S. Cl.
CPC ......... *C07D 213/79* (2013.01); *C07D 213/80* (2013.01); *C07D 233/96* (2013.01); *C07D 241/24* (2013.01); *C07D 401/06* (2013.01); *C12Q 1/485* (2013.01); *G01N 33/5041* (2013.01); *G01N 33/6893* (2013.01); *G01N 2333/70567* (2013.01)

(58) Field of Classification Search
CPC ....... C07D 401/06; C07C 63/74; C07C 65/26; C12Q 1/485; G01N 33/5041; G01N 33/6893; G01N 2333/70567
See application file for complete search history.

(56) References Cited

FOREIGN PATENT DOCUMENTS

| JP | S63243072 A | 10/1988 | | |
|---|---|---|---|---|
| WO | WO-2017152725 A1 * | 9/2017 | ........... | A61K 31/235 |
| WO | WO-2017174999 A1 * | 10/2017 | ........... | A61K 31/192 |

OTHER PUBLICATIONS

Francis-a-carey-organic-chemistry-4th-ed, p. 22 (Year: 2000).*
PubChem (https://pubchem.ncbi.nlm.nih.gov/#query=C21N2H2402&page=4) (Year: 2024).*
English translation of Examination Report issued for Japanese Patent Application No. JP2021-553136; (5 pages).
Chandraratna et al., "Development of RAR Subtype Selective Retinoids for Dermatological Diseases," European Journal of Medicinal Chemistry, vol. 30, No. Supplementary, 1995, pp. 505s-517s.
Chen et al., "Inhibition of Cancer Stem cell like Cells by a Synthetic Retinoid," Nature Communications, vol. 9, Article No. 1406, 2018; available from https://www.nature.com/articles/s41467-018-03877-7.
Gambone, Carlo J., et al.; "Unique Property of Some Synthetic Retinoids: Activation of the Aryl Hydrocarbon Receptor Pathway"; Molecular Pharmacology; (2002); vol. 61; No. 2; pp. 334-342.
Gluyas, Josef B.G., et al.; "Disila-analogues of the synthetic retinoids EC23 and TTNN: synthesis, structure and biological evaluation"; Organic & Biomolecular Chemistry; (2012); vol. 10; pp. 6914-6929.
Khatib, Thabat, et al.; "Genomic and Non-Genomic Pathways are both crucial for peak induction of neurite outgrowth by retinoids"; Celll Communication and Signalling; (2019); vol. 17; (16 pages).
Masía, Susana, et al.; "Rapid, Nongenomic Actions of Retinoic Acid on Phosphatidylinositol-3-Kinase Signaling Pathway Mediated by the Retinoic Acid Receptor"; Molecular Endocrinology; (2007); vol. 10; pp. 2391-2402.
PCT International Search Report and PCT Written Opinion for PCT International Patent Application No. PCT/GB2020/050607; mailing date Apr. 11, 2020; (17 pages).

* cited by examiner

SYNTHETIC RETINOIDS FOR USE IN RAR ACTIVATION

CROSS REFERENCE TO RELATED APPLICATIONS

This is the national phase under 35 U.S.C. § 371 of International Application No. PCT/GB2020/050607 filed on Mar. 11, 2020, which claims priority to and the benefit of Great Britain Patent Application No. 1903242.4 filed on Mar. 11, 2019, the entire disclosures of each are incorporated by reference herein.

The present invention relates to compounds of formula I:

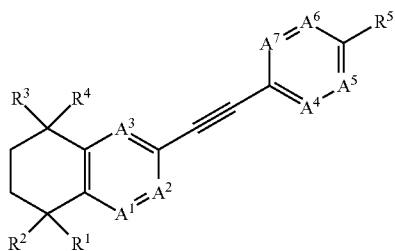

I in which $A^1$-$A^2$ and $R^1$ to $R^5$ are defined herein, for use in the treatment of a condition or disease which is alleviated by the activation of retinoic acid receptors (RAR). The invention also relates to pharmaceutical compounds comprising such compounds, and related methods of treatment. In an aspect, the invention relates to a method of screening compounds for therapeutic potential in the treatment of a condition or disease which is alleviated by the activation of retinoic acid receptors (RAR). In aspects, the present invention relates to novel compounds of formula I in which at least one of $A^1$ to $A^3$ is N, or at least one of $A^4$ is $CR^{12}$ or $A^5$ is $CR^{13}$ in which $R^{12}/R^{13}$ is halogen.

More particularly, the invention relates to the use of compounds of formula I in the treatment of conditions and/or diseases which are alleviated by the activation of RARs, such as neurological conditions, including neurodegenerative disorders such as Amyotrophic Lateral Sclerosis (ALS), Alzheimer's disease and Parkinson's disease, and conditions such as spinal cord injury.

Retinoids are a family of natural or synthetic compounds that are analogues of Vitamin A and its derivatives. Retinoids are essential for numerous cellular activities and as signalling molecules are involved in controlling important biological pathways from embryogenesis, through to adult homeostasis, as well as in aspects of stem cell development such as proliferation, differentiation and apoptosis. All-trans-retinoic acid (ATRA) is the most abundant endogenous retinoid and has been used as a model compound for the study of retinoids.

Retinoids act on a group of nuclear receptors known as retinoic acid receptors (RARs); inducible ligand-activated transcription factors which regulate multiple physiological mechanisms at a genomic level. Consequently, synthetic retinoids have been investigated as potential therapeutics for use in a range of diseases and conditions mediated or potentially mediated by RARs. However, to date known compounds have suffered from disadvantages such as low potency or efficacy, or have exhibited poor physical properties, including low aqueous solubility.

Neurological conditions are diseases of the central and peripheral nervous systems, i.e. the brain, spinal cord, cranial nerves, peripheral nerves, nerve roots, autonomic nervous system, neuromuscular junction and muscles. Neurological conditions include sudden onset conditions such as those resulting from spinal cord injury or stroke; intermittent conditions such as epilepsies; neurodegenerative conditions such as Amyotrophic Lateral Sclerosis (ALS), Alzheimer's disease and Parkinson's disease; and stable conditions such as cerebral palsy. Together, the group of neurological conditions tend to be chronic; many are life-threatening, and all have a significant negative impact on quality of life. In total, it is estimated that hundreds of millions of people worldwide are affected by neurological disorders (World Health Organisation, May 2016).

Amyotrophic Lateral Sclerosis (ALS), also known as Lou Gehrig's disease, is a debilitating neurological condition which is characterised by the progressive loss of motor neurons and resulting paralysis. In Europe, there are an estimated 1.7 to 2.3 cases of ALS per 100,000 population per year [Logroscino et al. "Incidence of amyotrophic lateral sclerosis in Europe". *J Neurol Neurosurg. Psychiatry.* (2009); 81(4): 385-90], and it is estimated that approximately 50% of patients die within 30 months of symptom onset [Kiernan et al. "Amyotrophic lateral sclerosis." The lancet; Vol. 377(9769); (2011): 942-955]. However, despite the devastating nature of the disease, there is presently no cure; the only drug approved in the United Kingdom for treatment of ALS has been shown to prolong patient life by on average two to three months [Miller et al. "Riluzole for amyotrophic lateral sclerosis (ALS)/motor neuron disease (MND)." Cochrane Database of Systematic Reviews (2012), Issue 3. CD001447].

ALS can be both sporadic and familial, with causative mutations described in multiple genes such as C9ORF72 and SOD1. The underlying cause of ALS is death of the motor neurons that drive muscle movement, but to date the precise mechanism by which this occurs is unknown.

However, several mechanisms have been implicated, including (i) excitotoxicity; the toxic effect of neurotransmitters causing neurons to fire excessively; (ii) autophagy failure; loss of the cell's detoxification system which removes the build-up of insoluble molecules in the cell; (iii) neuroinflammation; the mistaken attack of motor neurons by the immune cells of the nervous system; and (iv) axonal disorganisation; loss of the interconnecting fibres between neurons essential for their communication. Consequently, any therapeutic for use in the treatment of ALS would ideally exhibit polypharmocological properties.

There is consequently a dire and unmet need for new therapeutics for use in the treatment of neurological conditions, such as neurodegenerative disorders including ALS and Alzheimer's disease. Compounds which exhibit good physical properties, such as good aqueous solubility, would be particularly useful.

Whilst a therapeutic that could cure or prevent ALS, Alzheimer's disease or associated disorders represents the ultimate goal of most pharmaceutical research projects, more realistically, a therapeutic which could delay onset, slow down, or halt progression of the disease would represent a significant development. A method of screening compounds for potential therapeutic use would also be highly beneficial.

SUMMARY OF THE INVENTION

Accordingly, the present invention relates to compounds for use in the treatment of conditions or diseases which are alleviated by the activation of retinoic acid receptors. In aspects this includes genomic activation. In aspects of the invention, the compounds activate both genomic and non-genomic pathways.

In aspects, the invention relates to pharmaceutical compositions comprising such compounds, and to the use of such compounds and compositions in the treatment of conditions or diseases which are alleviated by the activation of retinoid acid receptors.

Conditions or diseases which are alleviated by the activation of retinoic acid receptors include conditions mediated by RAR, such as neurodegenerative disorders, as well as those which are alleviated by the activation of RAR, such as stroke, traumatic brain injury, epilepsy, spinal cord injury etc.

In aspects, the invention relates to methods of screening compounds for therapeutic potential in the treatment of conditions or diseases which are alleviated by the activation of retinoic acid receptors.

Aspects of the invention relate to novel compounds per se.

Further aspects and embodiments of the invention are as defined in the claims, and described in more detail below.

According to a first aspect of the present invention there is provided a compound of formula

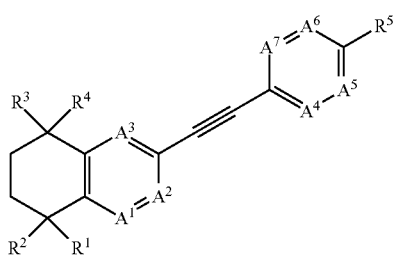

I in which:
$A^1$ is N or $CR^6$;
$A^2$ is N or $CR^7$;
$A^3$ is N or $CR^8$;
$R^6$ and $R^8$, are each independently hydrogen, $C_1$-$C_{10}$ alkyl, F, Br or Cl;
$R^7$ is independently hydrogen, $C_1$-$C_{10}$ alkyl, F, Br, Cl or —$OCR^9$ in which $R^9$ is H or $C_1$-$C_6$ alkyl;
$R^1$ to $R^4$ are each independently $C_1$-$C_{10}$ alkyl, or $R^1$ and $R^2$ and/or $R^3$ and $R^4$ join to form a 3-membered ring;
$A^4$ is N or $CR^{12}$;
$A^5$ is N or $CR^{13}$;
$A^6$ is N or $CR^{14}$;
$A^7$ is N or $CR^{15}$;
each $R^{12}$ to $R^{15}$ is independently H, halogen or haloalkyl $C_1$-$C_{10}$; and
$R^5$ is —$C(=O)R^{16}$ or —$C(=O)OR^{16}$ in which $R^{16}$ is H or $C_{1-10}$ alkyl;
with the proviso that at least one of $A^1$ to $A^7$ is N or at least one of $R^{12}$ to $R^{15}$ is F, Cl or Br;
and isomers thereof;
in free or in salt form;
for use in the treatment of a condition or disease which is alleviated by the activation of retinoic acid receptors (RAR).

In the compound of formula I, at least one of $A^1$ to $A^7$ is N or at least one of $R^{12}$ to $R^{15}$ is F, Cl or Br.

As used herein, the term "alkyl" refers to a fully saturated, branched, unbranched or cyclic hydrocarbon moiety, i.e. primary, secondary or tertiary alkyl or, where appropriate, cycloalkyl or alkyl substituted by cycloalkyl. Where not otherwise indicated, an alkyl group comprises 1 to 10 carbon atoms, preferably 1 to 6 carbon atoms, or more preferably 1 to 4 carbon atoms. Representative examples of alkyl groups include, but are not limited to, methyl, ethyl, n-propyl, iso-propyl, n-butyl, sec-butyl, iso-butyl, Cert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "halogen" or "halo" as used herein, means fluoro, chloro, bromo, or iodo.

As used herein the term "haloalkyl" refers to an alkyl group in which one or more hydrogen atoms are replaced by a halogen atom.

Conditions or diseases which are alleviated by the activation of retinoic acid receptors include conditions mediated by RAR, such as neurodegenerative disorders, as well as those which are alleviated by the activation of RAR, such as stroke, traumatic brain injury, epilepsy, spinal cord injury etc.

RAR-mediated conditions include neurodegenerative disorders, including Amyotrophic lateral sclerosis (ALS), neuromuscular disease, Parkinson's disease, multiple sclerosis (MS), Alzheimer's disease, early-stage Alzheimer's disease, intermediate-stage Alzheimer's disease, late-stage Alzheimer's disease, cognitive disorders, memory impairment, memory deficit, senile dementia, vascular dementia, cognitive impairment, and mild cognitive impairment.

Accordingly, the condition or disease alleviated by the activation of RAR may be selected from Amyotrophic lateral sclerosis (ALS), neuromuscular disease, Parkinson's disease, multiple sclerosis (MS), Alzheimer's disease, early-stage Alzheimer's disease, intermediate-stage Alzheimer's disease, late-stage Alzheimer's disease, cognitive disorders, memory impairment, memory deficit, senile dementia, vascular dementia, cognitive impairment, mild cognitive impairment, stroke, traumatic brain injury, epilepsy and spinal cord injury.

The condition may be a neurological condition. In embodiments, the neurological condition may be a neurodegenerative condition, such as ALS, Parkinson's disease or Alzheimer's disease.

In an embodiment, $R^5$ is —COOH.

In an embodiment, at least one of $A^1$ to $A^3$ is N or at least one of $A^4$ is $CR^{12}$ or $A^5$ is $CR^{13}$ in which $R^{12}/R^{13}$ is halogen. $R^{12}/R^{13}$ is preferably F.

In an embodiment, at least one of $A^1$ to $A^3$ is N. In an embodiment, $A^1$ and $A^3$ are both N.

In an embodiment, $A^2$ is $CR^7$ in which $R^7$ is H.

In an embodiment, at least one of $A^4$, $A^5$ or $A^6$ is CF.

In this embodiment, $A^4$ may be CF. Alternatively, $A^5$ may be CF.

In an embodiment, $A^5$ and $A^6$ are CF.

In an embodiment, $A^4$ is CCl.

In an embodiment $A^1$ and $A^3$ are both N and $A^2$ is $CR^7$ in which $R^7$ is H, as represented by formula IA:

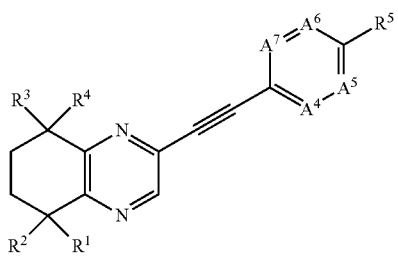

IA

Preferably, in formula IA, R⁵ is —COOH.

Alternatively, in an embodiment, in formula I, at least one of $A^4$ to $A^7$ is N.

In an embodiment, in formula I, $A^4$ is N.

In an embodiment, in formula I, $A^4$ or $A^5$ is CF.

In general terms, the compound of formula I has a hydrophobic region, a linker region (—C≡C—) and a polar region, as shown below:

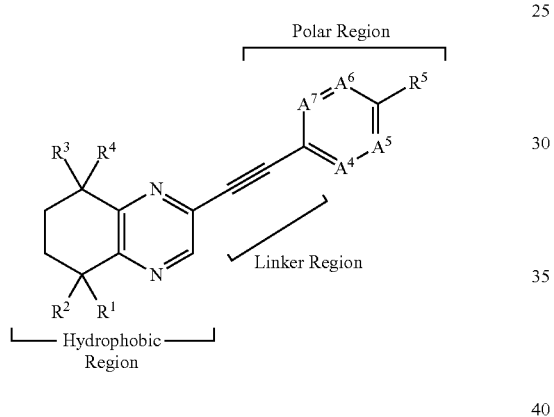

The inventors have advantageously discovered that compounds of formula I, in which one, or preferably two nitrogen atoms are incorporated in the conjugated ring of the hydrophobic region; or in which a nitrogen atom is incorporated in the conjugated ring of the polar region and/or the conjugated ring of the polar region is halogenated (or preferably fluorinated), may be surprisingly beneficial in the treatment of diseases or conditions that are alleviated by the activation of RAR.

Illustrative compounds of formula I which may be mentioned include those selected from the group consisting of:

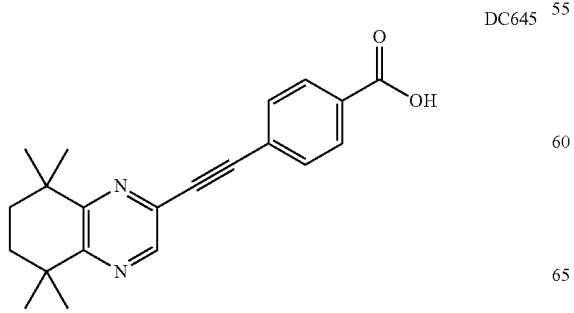

DC645

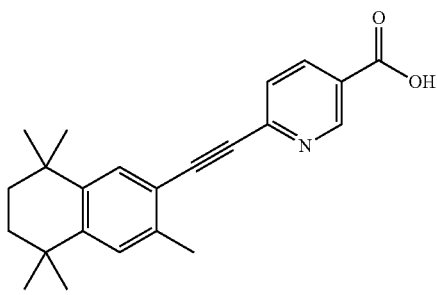

DC656

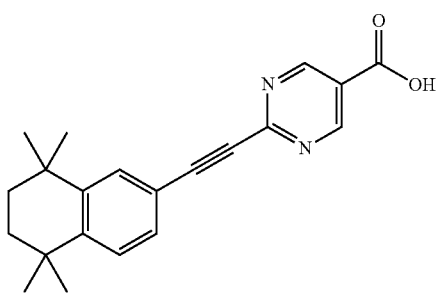

DC708

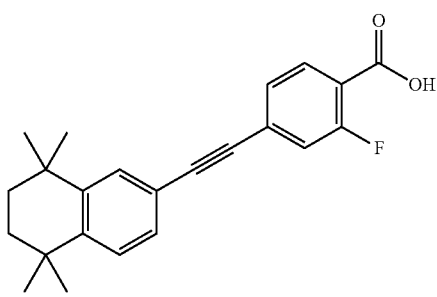

DC525

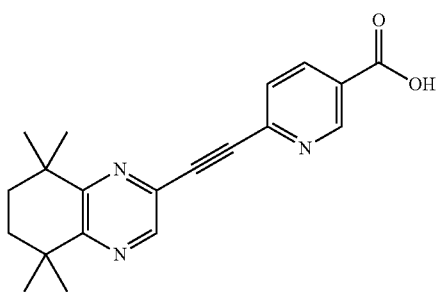

DC650

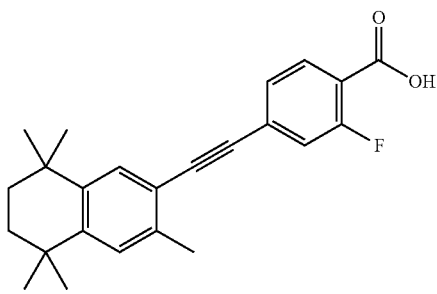

DC667

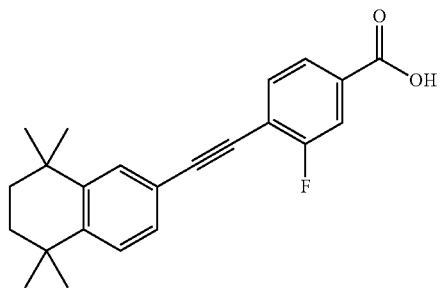
DC526
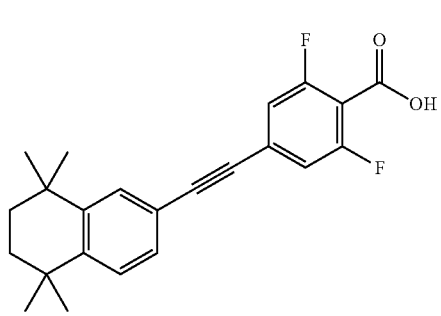
DC540
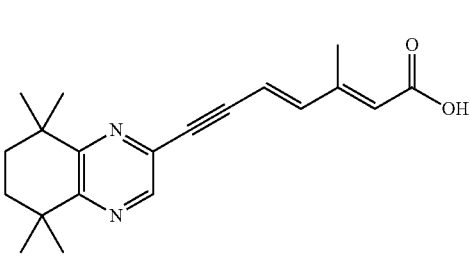
DC670
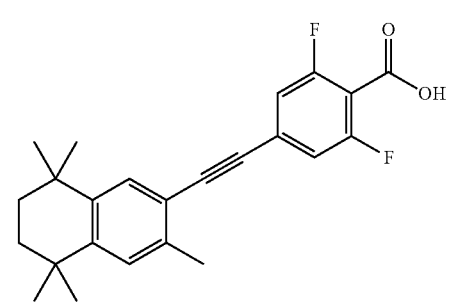
DC661
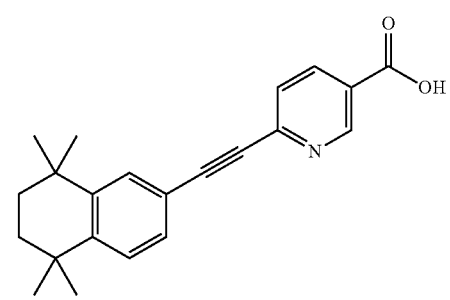
DC527
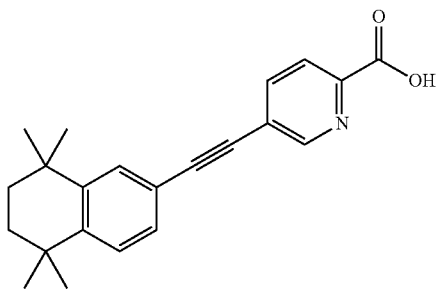
DC528
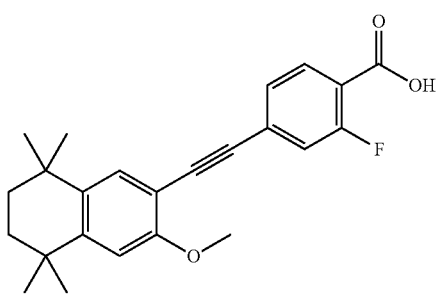
DC673
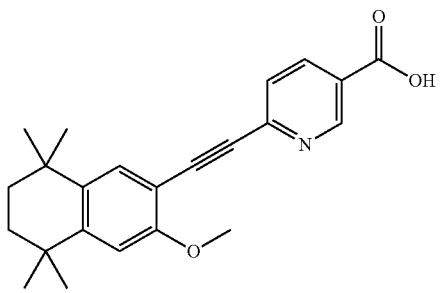
DC646
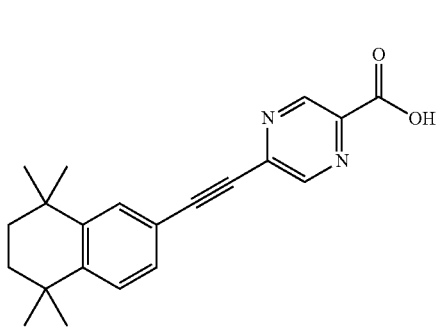
DC529
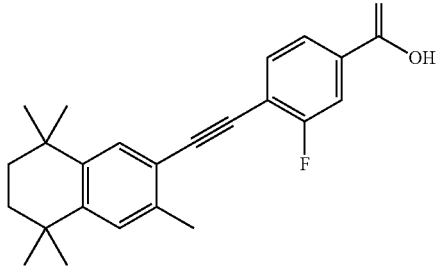
DC559

DC657
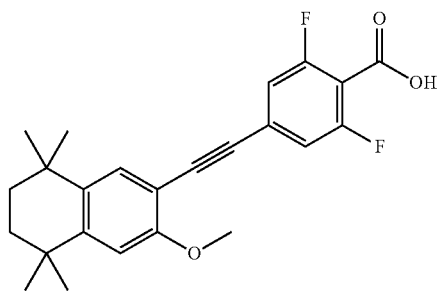
DC567
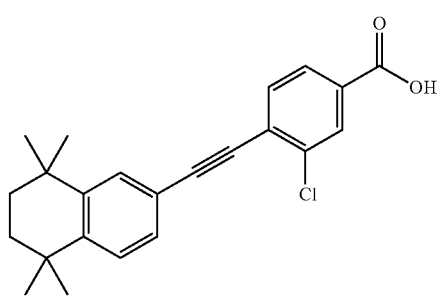
DC564
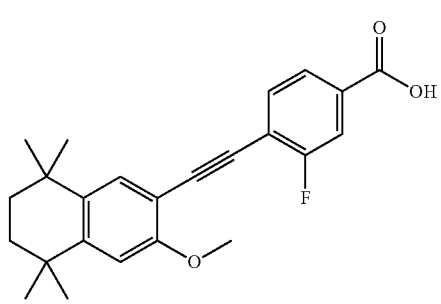
DC702
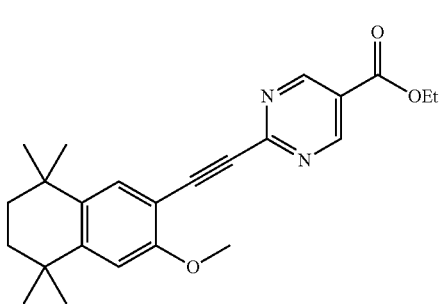
DC706
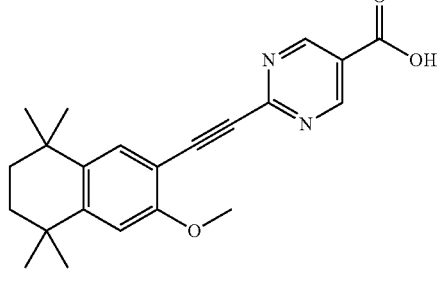
DC707
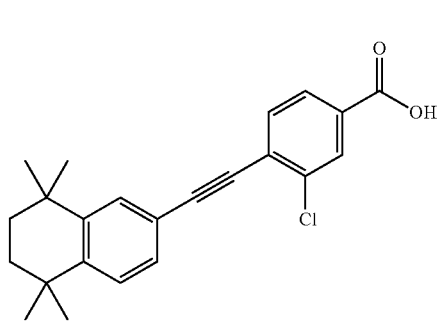
DC712
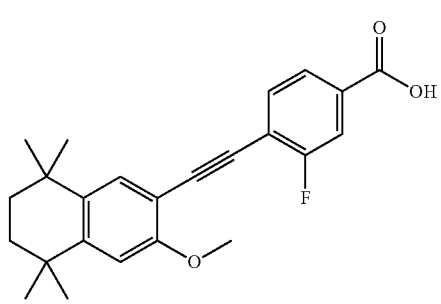
DC641
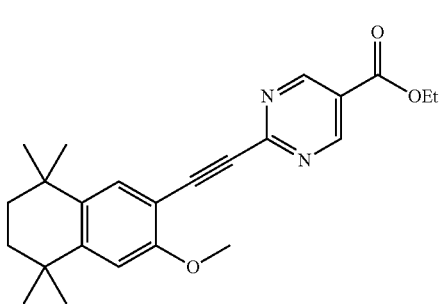
In particular embodiments, the compound of formula I may be selected from:
DC645
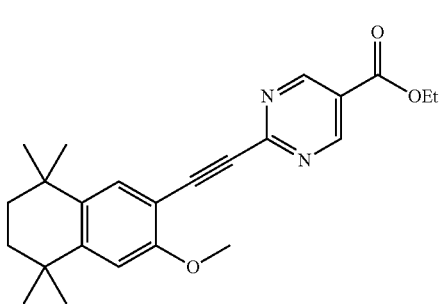
DC656
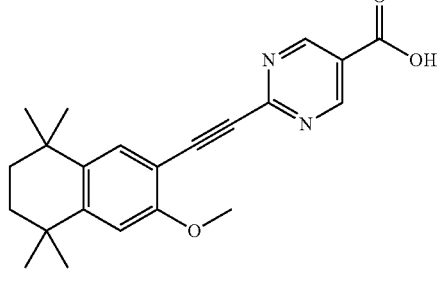

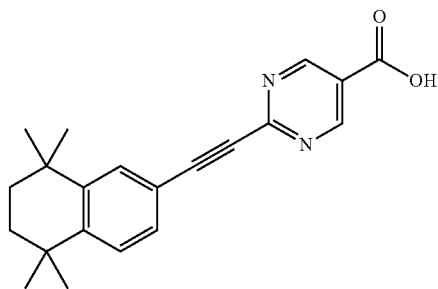
DC708
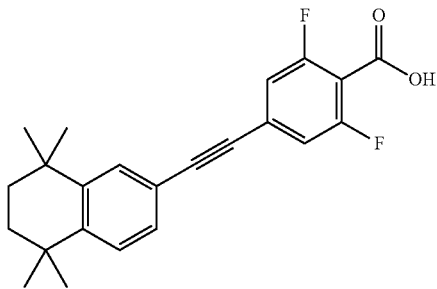
DC540
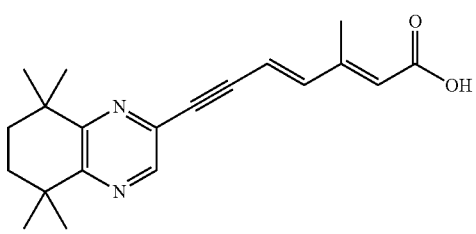
DC525
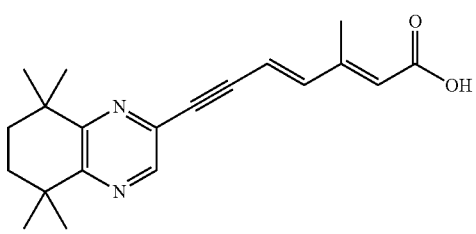
DC670
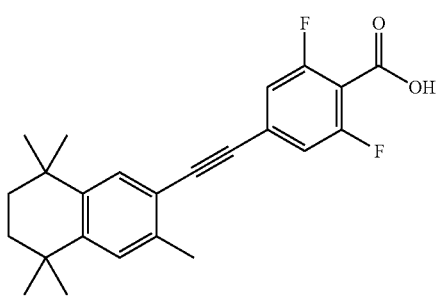
DC650
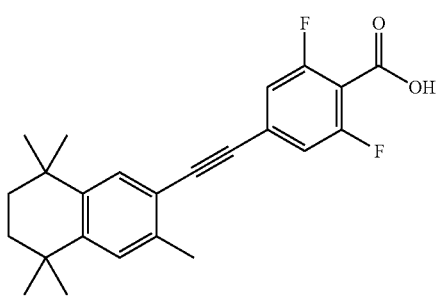
DC661
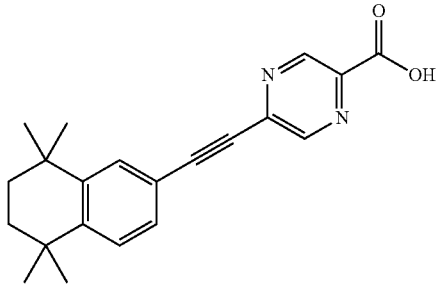
DC667
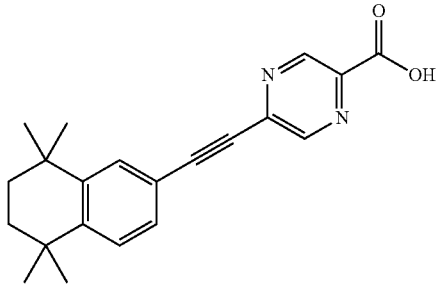
DC529
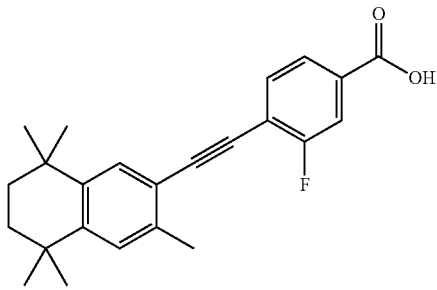
DC526
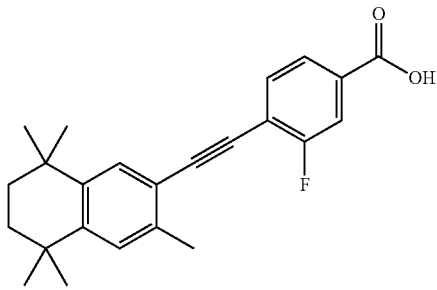
DC559

-continued
DC673
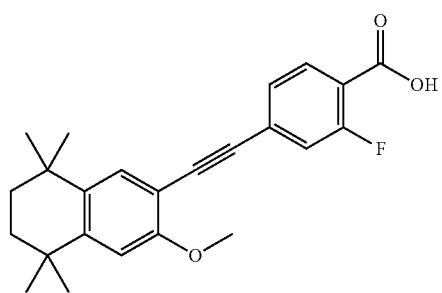
DC646
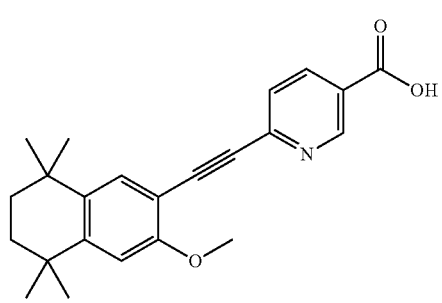
DC564
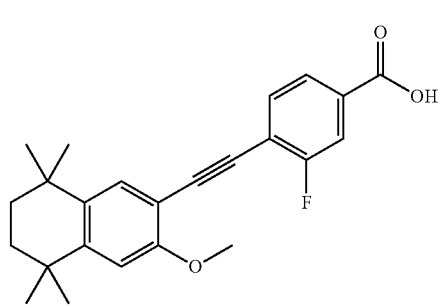
DC702
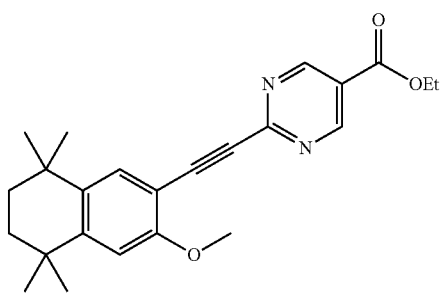
DC657
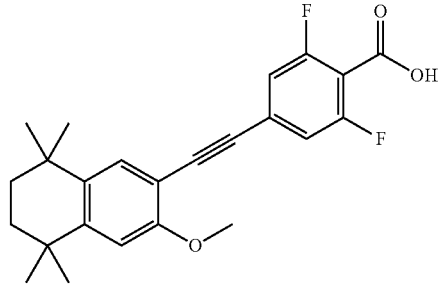
-continued
DC567
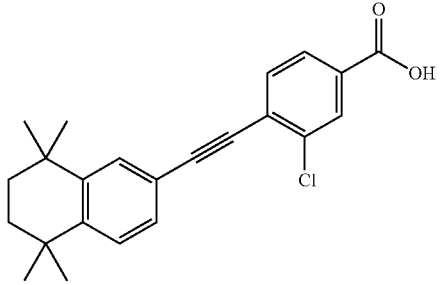
DC712
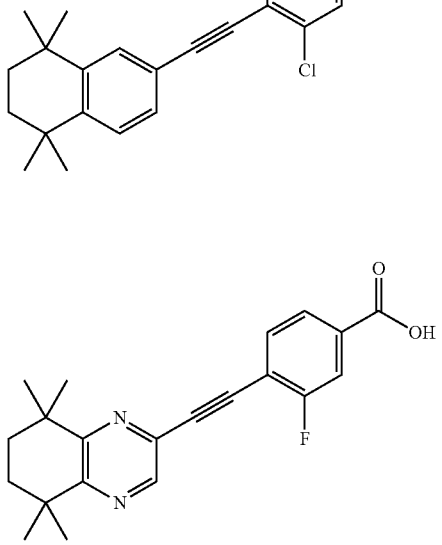
DC641
DC706
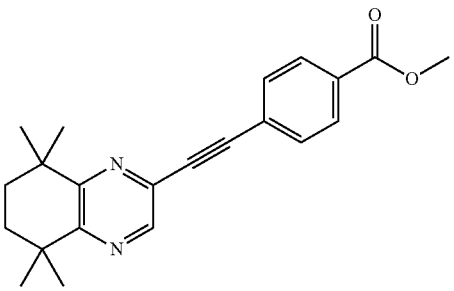
DC707
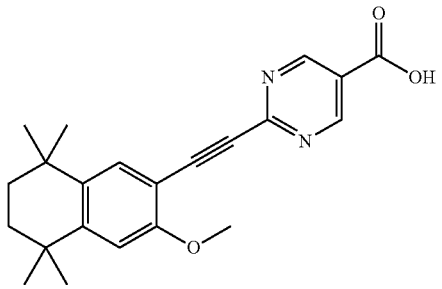
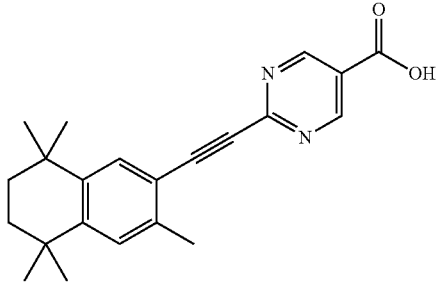
In embodiments, the compound of formula I may be selected from:

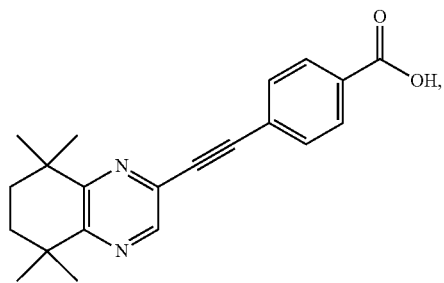 [SMILES: CC1(C)CCC(C)(C)c2cc(C#Cc3ccc(C(=O)O)cc3)ccc21]
DC645

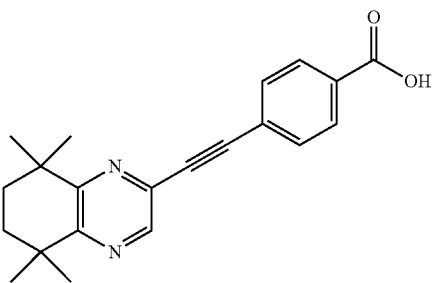
DC645

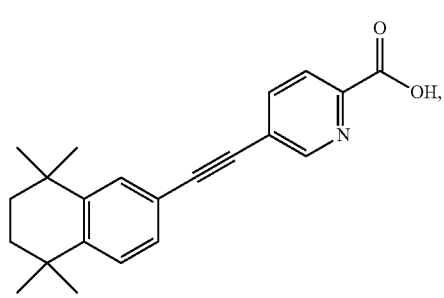 [SMILES: CC1(C)CCC(C)(C)c2cc(C#Cc3ccc(C(=O)O)cc3)ccc21]
DC528

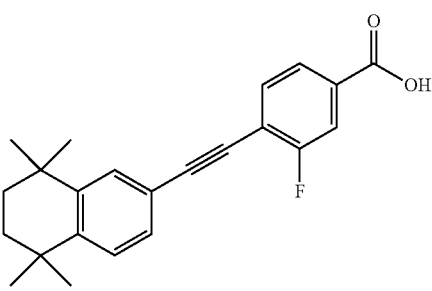
DC526

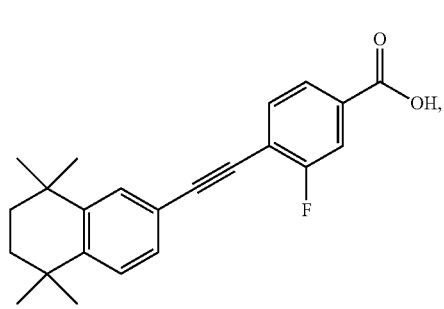
DC526

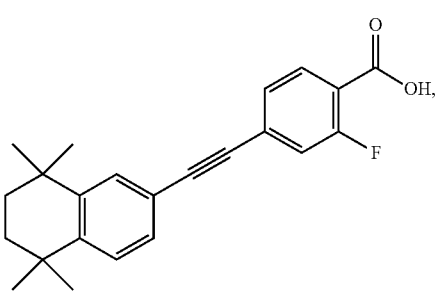
DC525

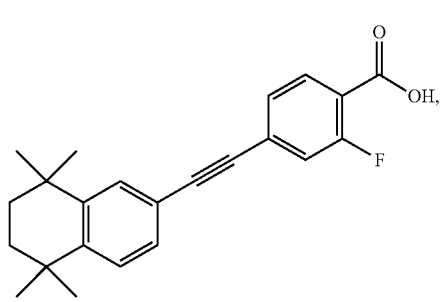
DC525

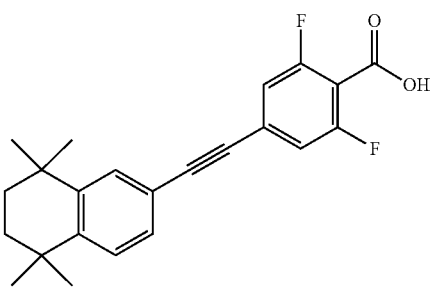
DC540

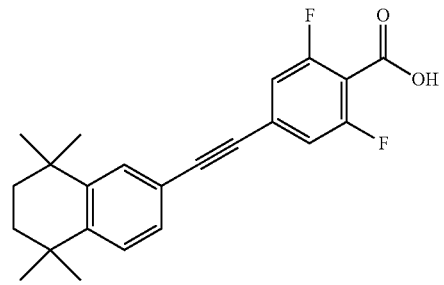
DC540

In embodiments, the compound of formula I may be selected from:

In another aspect of the present invention there is provided the use of a compound of formula I, as defined herein, in the manufacture of a medicament for use in the treatment of a disease or condition which is alleviated by the activation of RAR. In an embodiment, the medicament comprises a compound of formula I.

In another aspect of the present invention there is provided a method of treatment of a patient with a disease or condition which is alleviated by the activation of RAR, the method comprising administering to a patient a therapeutically effective amount of a compound of formula I, wherein the compound of formula I is as defined herein.

In another aspect of the present invention there is provided a pharmaceutical composition comprising a compound of formula I as defined herein, optionally in conjunction with one or more pharmaceutically acceptable excipients, diluents or carriers, for use in the treatment of a disease or condition which is alleviated by the activation of RAR. The composition may optionally comprise one or more additional therapeutic agents.

The term "therapeutically effective" amount, or "effective amount" refers to a quantity of the compound or composition of the present invention which is effective in producing the desired therapeutic, ameliorative, inhibitory or preventative effect.

The term "pharmaceutical composition" refers to a composition suitable for administration to a patient. Thus, the term "pharmaceutical composition" refers to compositions which comprise the compound of the invention or mixtures thereof, or salts, solvates, prodrugs, isomers or tautomers thereof, optionally in combination with one or more pharmaceutically acceptable excipients, carriers or diluents. The term "pharmaceutical composition" is also intended to encompass both the bulk composition (i.e. in a form that has not yet been formed into individual dosage units) and individual dosage units. Such individual dosage units include tablets, pills, caplets, ampoules and the like.

Those skilled in the art will recognize those instances in which the compounds of the invention may be converted to prodrugs and/or solvates. The term "prodrug" refers to a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood.

The compounds of the invention may be unsolvated or may be solvated with pharmaceutically acceptable solvents such as water, ethanol, and the like. For instance, it will be understood that a solvate may be capable of isolation, for example when one or more solvent molecules are incorporated in the crystal lattice of the crystalline solid. "Solvate" encompasses both solution-phase and isolatable solvates. Suitable solvates include, but are not limited to, ethanolates, methanolates, hydrates, and the like.

Compounds for use in the invention include salts thereof, and reference to a compound of the invention is intended to include reference to salts thereof, unless otherwise stated. Suitable salts include for instance, acidic salts formed with inorganic and/or organic acids, basic salts formed with inorganic and/or organic bases, as well as zwitterions ("inner salts") which may be formed and are included within the term "salt(s)" as used herein. Pharmaceutically acceptable (i.e., non-toxic, physiologically acceptable) salts are preferred, although other salts may be useful in certain circumstances. Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates) and the like. Exemplary basic salts which may be useful include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternerized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), arylalkyl halides (e.g. benzyl and phenethyl bromides), and others.

Compounds for use in the invention include pharmaceutically acceptable esters thereof, and may include carboxylic acid esters, obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$ alkyl, or $C_{1-4}$ alkoxy or amino); (2) sulfonate esters, such as alkyl- or aralkylsulfonyl (for example, methanesulfonyl); (3) amino acid esters (for example, L-valyl or L-isoleucyl); (4) phosphonate esters; and (5) mono-, di- or triphosphate esters.

Polymorphic forms of the compounds of the invention, and of the salts, solvates, esters and prodrugs of the compounds of the invention, are intended to be included in the present invention.

Suitable dosages for administering compounds of the invention to patients may be determined by those skilled in the art, e.g. by an attending physician, pharmacist, or other skilled worker and may vary according to factors such as patient weight, health, age, frequency of administration, mode of administration, the presence of any other active ingredients, and the condition for which the compounds are being administered.

Examples of excipients, diluents and carriers include buffers, as well as fillers and extenders such as starch, cellulose, sugars, mannitol and silicic derivatives. Binding agents may also be included. Adjuvants may also be included.

Optionally the compound of formula I may be administered in combination with one or more additional therapeutic agents. When used in combination with one or more additional therapeutic agents, the compounds of the invention may be administered together or sequentially.

The compositions may be administered by a variety of routes including oral, parenteral (including subcutaneous, intravenous, intramuscular and intraperitoneal), rectal, dermal, transdermal, intrathoracic, intrapulmonary, mucosal, intraocular and intranasal routes.

Suitable dosage forms will be recognised by one skilled in the art and include, among others, tablets, capsules, solutions, suspensions, powders, aerosols, ampules, pre-filled syringes, small volume infusion containers or multi-dose containers, creams, milks, gels, dispersions, microemulsions, lotions, impregnated pads, ointments, eye drops, nose drops, lozenges etc.

Aspects of the invention relate to compounds of formula I as hereinbefore described in which at least one of $A^1$ to $A^3$ is N or at least one of $A^4$ is $CR^{12}$ or $A^5$ is $CR^{13}$ in which $R^{12}/R^{13}$ is halogen. Such aspects relate to the novel compounds per se.

$R^{12}/R^{13}$ is preferably F.

In an embodiment at least one of $A^1$ to $A^3$ is N.

In an embodiment, $A^1$ and $A^3$ are both N.

In an embodiment, the novel compound is selected from:
DC645
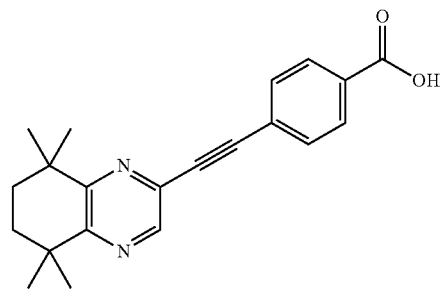
DC525
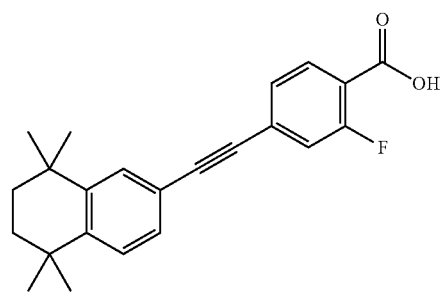
DC540
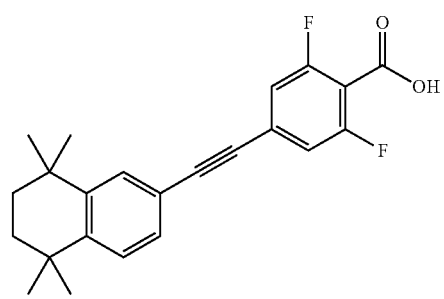
DC650
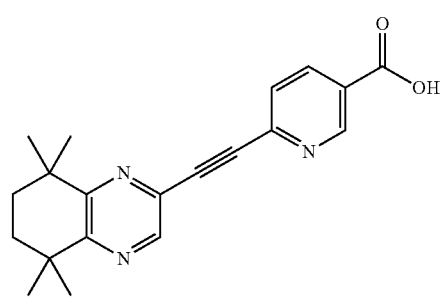
DC667
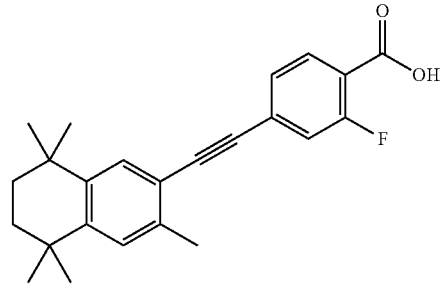
DC526
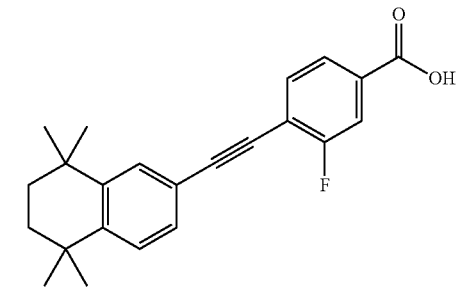
DC670
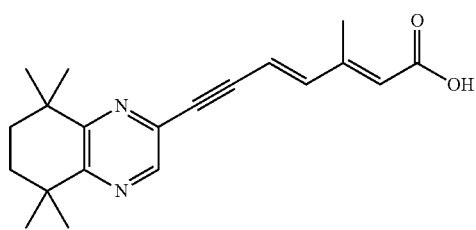
DC661
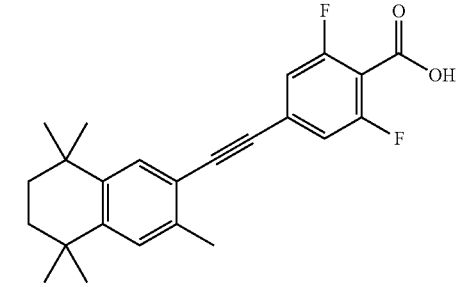
DC559
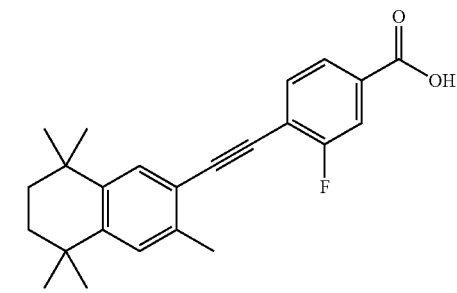
DC673
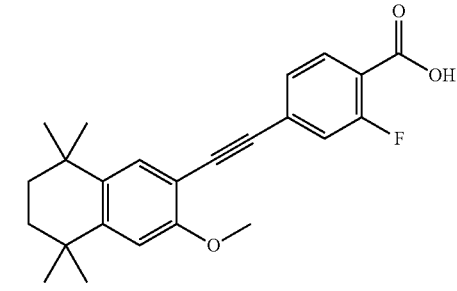

-continued

DC567
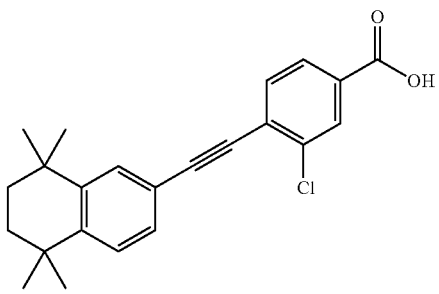

DC564
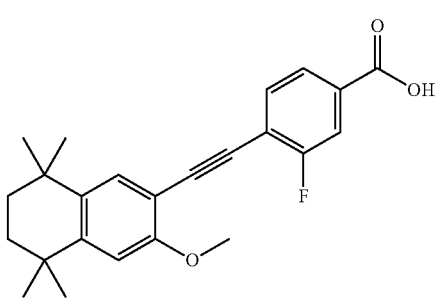

DC657
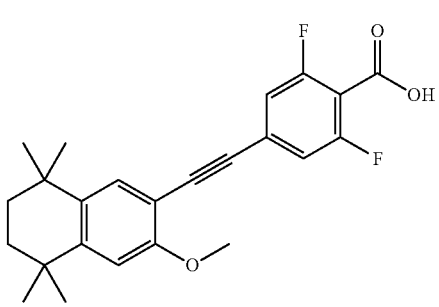

DC712
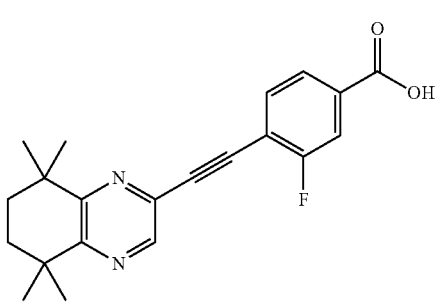

DC641
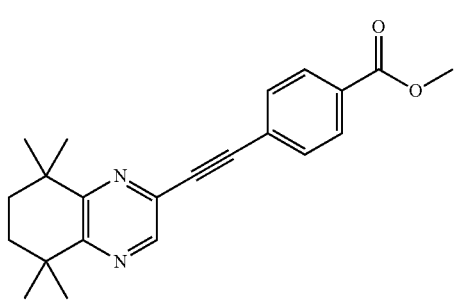

In an aspect of the present invention there is provided a method of screening compounds for therapeutic potential in the treatment of conditions or diseases which are alleviated by the activation of retinoic acid receptors, the method comprising:

performing an assay to determine the efficacy ($E_{max}$) of a compound in activating a RAR as an indicator of genomic activity;

performing an assay to determine the efficacy ($E_{max}$) of a compound as an indicator of non-genomic activity;

for each assay, comparing the $E_{max}$ to a baseline value; and, selecting those compounds which have an $E_{max}$ above the baseline value in both assays for further investigation.

Since the discovery of RARs as members of the nuclear receptor family of transcriptional regulators (Petkovich M et al. "A human retinoic acid receptor which belongs to the family of nuclear receptors"; Nature (1987): 330, pp. 444-450], the emphasis on retinoid function has been on their control of gene expression. On this basis, synthetic retinoids have been generated and investigated for their genomic activating properties.

Surprisingly, however, the inventors have determined that genomic and non-genomic mechanisms of retinoid acid (RA) are regulated independently with respect to the involvement of ligand-dependent RARs. "Dual-efficacy", i.e. activity in both non-genomic and genomic assays, has been found to correlate strongly with promotion of neurite outgrowth and increased cell number and survival, suggesting that these dual-effect compounds are significant as potential therapeutics.

In an embodiment, the assay to determine the $E_{max}$ of a compound as an indicator of non-genomic activity is a kinase phosphorylation assay.

In an embodiment, the kinase phosphorylation assay is an ERK1/2 phosphorylation assay.

In an embodiment, the baseline value as an indicator of genomic activity is an $E_{max}$ of 170.1.

In an embodiment, the baseline value as an indicator of non-genomic activity is an $E_{max}$ of 48.55.

One or both of the baseline values can, in embodiments, be determined using a reference compound, such as ATRA.

EXAMPLES

The invention will now be described by way of example only with reference to the accompanying figures, in which.

FIG. 8 compares the activity of exemplary retinoid DC645 with that of ATRA and EC23.

Figure 8A:
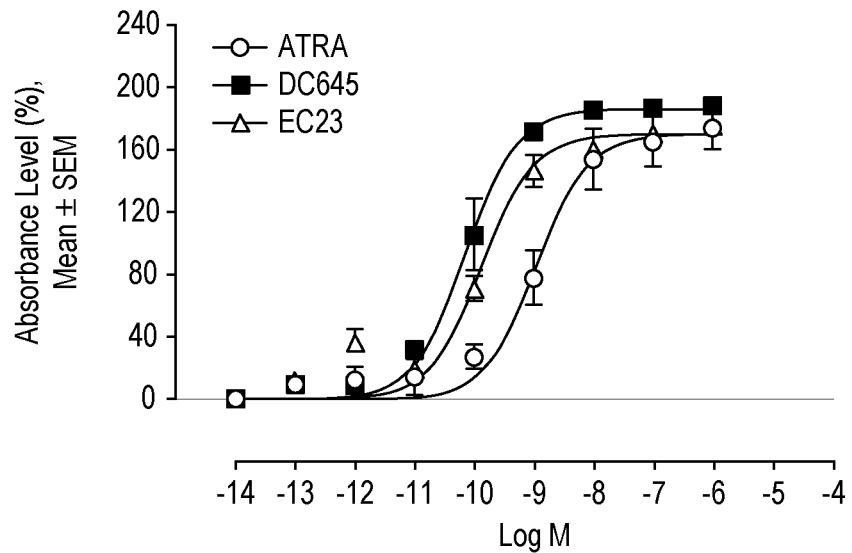
Figure 8B:
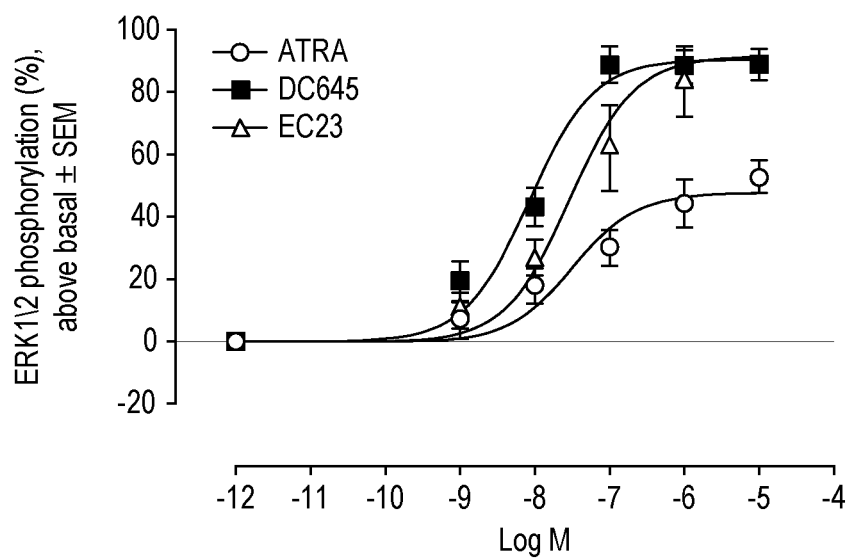
Figure 8C:
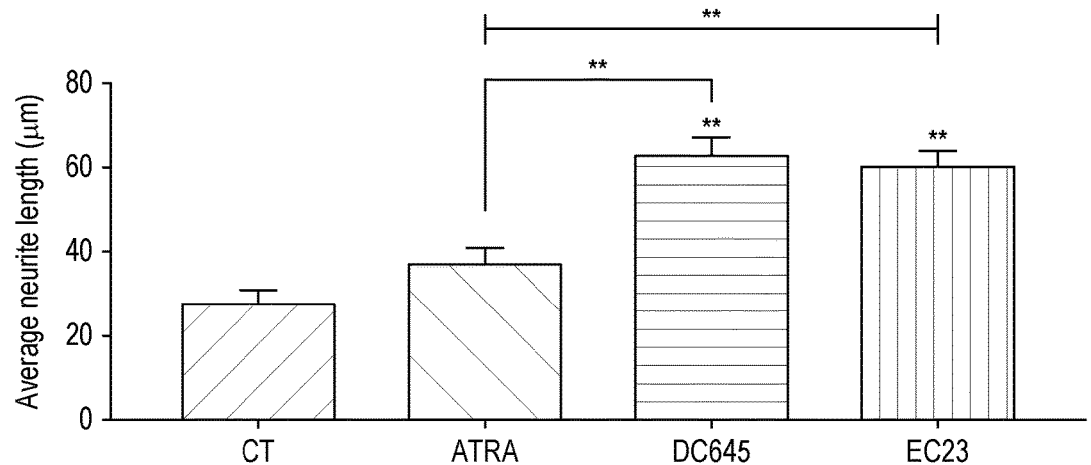
Figure 8D:
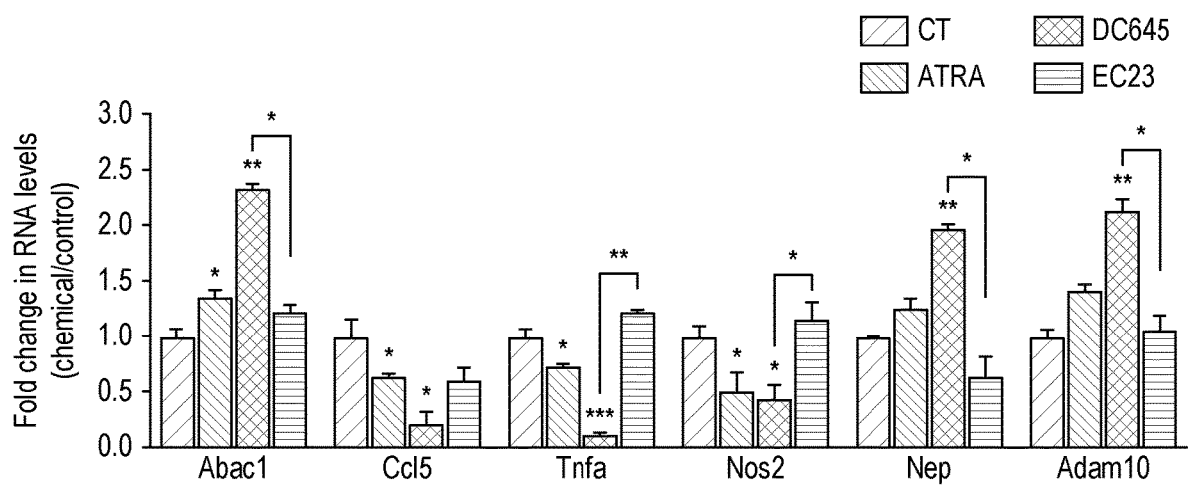

FIG. 8(a) compares the genomic activity of the retinoids by means of the X-Gal assay; FIG. 8(b) compares the non-genomic activity of the retinoids by measuring their ability to induce ERK 1/2 phosphorylation; FIG. 8(c) compares the ability of the compounds to induce neurite outgrowth in SH-SY5Y cells; and FIG. 8(d) shows the regulation of Alzheimer's disease-related genes by retinoid compounds.

EXAMPLE 1: SYNTHESIS OF EXEMPLARY COMPOUNDS OF FORMULA I

1.1 Synthesis of Coupling Partners

1.1.1. Synthesis of 6-Iodo-1,1,4,4-tetramethyl-1,2,3,4-tetrahydronaphthalene, 1

Figure 1A:
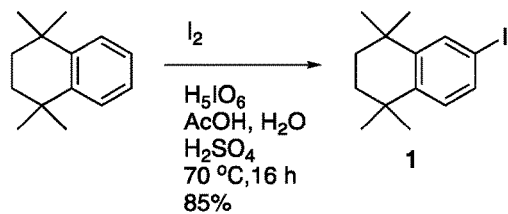
FIG. 1 illustrates the synthesis of coupling partners.

The synthesis of 6-Iodo-1,1,4,4-tetramethyl-1,2,3,4-tetrahydronaphthalene (1) is illustrated in FIG. 1(a). 1,1,4,4-Tetramethyl-1,2,3,4-tetrahydronaphthalene (11.46 g, 60.9 mmol), $I_2$ (7.77 g, 30.6 mmol) and $H_5IO_6$ (3.49 g, 15.3 mmol) were added to a mixture of gl. ethanoic acid/acetic acid (AcOH) (250 mL), $H_2O$ (25 mL), and $H_2SO_4$ (13 mL), and the resultant solution was stirred at 70° C. for 6 hours. The solution was cooled, and extracted with ethyl ethanoate/ethyl acetate (EtOAc). The organics were washed with sat. $Na_2S_2O_3$, $H_2O$ and brine, dried ($MgSO_4$) and evaporated to give a crude orange oil (17 g). This was purified by dry column vacuum chromatography (eluting with heptane) to give compound 1 as a white solid (16.3 g, 85%): 1H NMR (700 MHz, CDCl3) δ 1.25 (s, 6H), 1.26 (s, 6H), 1.66 (s, 4H), 7.04 (d, J=8.4 Hz, 1H), 7.43 (dd, J=8.4, 1.9 Hz, 1H), 7.60 (d, J=1.9 Hz, 1H); 13C NMR (176 MHz, CDCl3) δ 31.9, 32.0, 34.4, 34.6, 35.0, 35.1, 91.3, 128.9, 134.8, 135.8, 144.8, 147.9; all other data matched the literature (V. B. Christie et al, *Org. Biomol. Chem.*, 2008, 6, 3497-3507).

1.1.2 Synthesis of 6-Ethynyl-1,1,4,4-tetramethyl-1,2,3,4-tetrahydronaphthalene, 3

Figure 1B:
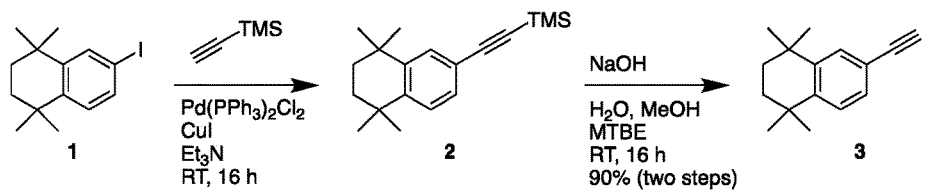

The synthesis of 6-ethynyl-1,1,4,4-tetramethyl-1,2,3,4-tetrahydronaphthalene (3) is illustrated in FIG. 1(b). Triethylamine ($Et_3N$) (150 mL) was degassed by sparging with $N_2$ for 1 h. Compound 1 (10.0 g, 31.8 mmol), $Pd(PPh_3)_2Cl_2$ (0.223 g, 0.32 mmol), CuI (0.061 g, 0.32 mmol) and trimethylsilylacetylene (5.29 mL, 38.2 mmol) were then added under $N_2$ and the resultant slurry was stirred at RT for 20 h. The mixture was diluted with heptane and passed through Celite/$SiO_2$ (eluting with heptane), and the resultant solution was evaporated to give a crude brown oil (10.36 g). This was purified by $SiO_2$ chromatography (100% heptane) to give compound 2 as a yellow oil (9.99 g, >100%). Compound 2 (9.99 g, 35.1 mmol) was dissolved in methanol (MeOH)/methyl tert-butyl ether (MTBE) (1:1, 160 mL). A solution of sodium hydroxide (NaOH) (0.96 g, 24.0 mmol) in $H_2O$ (15 mL) was then added and the resultant solution was stirred at RT for 16 h. The solution was diluted with MTBE, washed with $H_2O$ and brine, dried ($MgSO_4$) and evaporated to give a crude yellow oil (6.6 g). This was purified by $SiO_2$ chromatography (100% heptane) to give compound 3 as a colourless oil that slowly solidified (6.06 g, 90% over two steps): all data matched the literature (V. B. Christie et al, *Org. Biomol. Chem.*, 2008, 6, 3497-3507).

1.1.3 Synthesis of 4-bromo-3-fluorobenzoate, 4

Figure 1C:
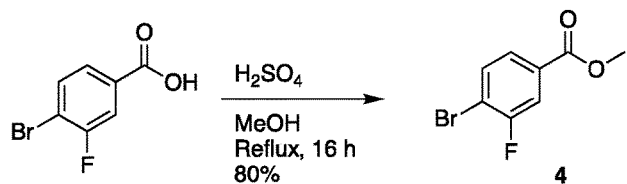

The synthesis of 4-bromo-3-fluorobenzoate (4) is illustrated in FIG. 1(c). 4-Bromo-2-fluorobenzoic acid (25.0 g, 114.2 mmol) was suspended in MeOH (250 mL), whereupon conc. $H_2SO_4$ (4 mL) was added and the resultant solution was stirred at reflux overnight. The clear solution was then cooled, and $H_2O$ (100 mL) was added, whereupon a white precipitate formed. This was filtered, washed with $H_2O$ and dried to give a crude white solid. This was recrystallised from heptane to give compound 4 as a colourless crystalline solid (21.34 g, 80%): $^1$H NMR (600 MHz, CDCl$_3$) δ 3.91 (s, 3H), 7.31-7.36 (m, 2H), 7.80 (t, J=8.0 Hz, 1H); $^{13}$C NMR (151 MHz, CDCl$_3$) δ 52.4, 117.6 (d, J=9.9 Hz), 120.6 (d, J=25.6 Hz), 127.5 (d, J=3.9 Hz), 127.9 (d, J=9.6 Hz), 133.1, 161.56 (d, J=264.9 Hz), 164.1 (d, J=3.9 Hz); $^{19}$F NMR (376 MHz, CDCl$_3$) δ −106.6; IR (ATR) $v_{max}$/cm$^{-1}$ 3104w, 3086w, 2961w, 1712s, 1599s, 1571m, 1403m, 1215s, 882s; MS (ASAP): m/z=233.0 [M+H]$^+$; HRMS (ASAP) calcd. for $C_3H_7O_2BrF$ [M+H]$^+$: 232.9613, found: 232.9621 (Zimmerman et al., *J. Med. Chem.* 2014, 57:2334-2356).

1.1.4 Synthesis of Methyl 4-ethynyl-3-fluorobenzoate, 6

Figure 1D:
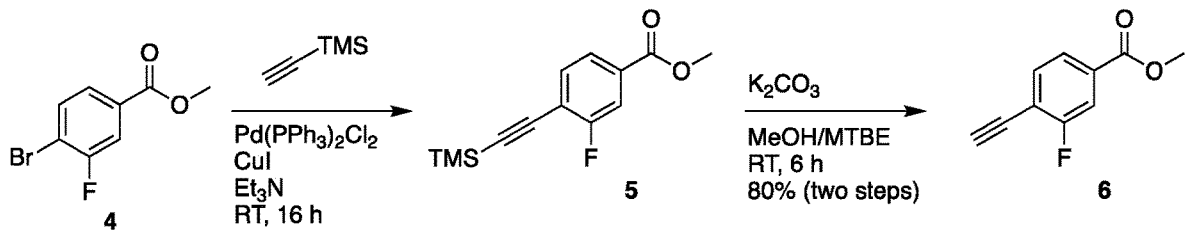

The synthesis of Methyl 4-ethynyl-3-fluorobenzoate (6) is illustrated in FIG. 1(d). $Et_3N$ (120 mL) was degassed by sparging with $N_2$ for 1 hour. Compound 4 (5.0 g, 21.45 mmol), trimethylsilylacetylene (3.56 mL, 25.74 mmol), $Pd(PPh_3)_2Cl_2$ (301 mg, 0.429 mmol) and CuI (82 mg, 0.429 mmol) were then added under $N_2$ and the resultant suspension was stirred at room temperature for 16 hours. The suspension was diluted with heptane and passed through Celite®/$SiO_2$ and the extracts were evaporated to a give a crude oil (6.44 g). This was purified by dry column vacuum chromatography (100% heptane, to 9:1, heptane/EtOAc), and the isolated product further purified by Kugelrohr distillation (150° C., 7.4 Torr) to give compound 5 as a yellow oil (5.58 g, >100%) which was carried directly to the next step: $^1$H NMR (400 MHz, CDCl$_3$) δ 0.27 (s, 9H), 3.92 (s, 3H), 7.50 (dd, J=8.0, 6.8 Hz, 1H), 7.71 (dd, J=9.6, 1.5 Hz, 1H), 7.75 (dd, J=8.0, 1.6 Hz, 1H). To a MeOH:MTBE solution (5:50, 55 mL) was added compound 5 (5.58 g, 22.3 mmol) and $K_2CO_3$ (6.16 g, 44.6 mmol), and the resultant mixture was stirred under $N_2$ for 6 hours at room temperature. The solution was then diluted with EtOAc, washed with sat. $NH_4Cl$, $H_2O$ and brine, dried ($MgSO_4$) and evaporated to give a crude solid (3.6 g). This was purified by dry column vacuum chromatography (100% heptane, to 8:2, heptane/EtOAc) to give compound 6 as a white solid (3.07 g, 80% over two steps): $^1$H NMR (600 MHz, CDCl$_3$) δ 3.45 (s, 1H), 3.92 (s, 3H), 7.53 (dd, J=8.0, 6.8 Hz, 1H), 7.72 (dd, J=9.6, 1.6 Hz, 1H), 7.77 (dd, J=8.0, 1.6 Hz, 1H); $^{13}$C NMR (151 MHz, CDCl$_3$) δ 52.5, 76.3, 85.1 (d, J=3.3 Hz), 115.3 (d, J=16.0 Hz), 116.5 (d, J=22.9 Hz), 124.9 (d, J=3.7 Hz), 132.2 (d, J=7.4 Hz), 133.9 (d, J=1.3 Hz), 162.9 (d, J=253.5 Hz), 165.3 (d, J=2.7 Hz); $^{19}$F NMR (376 MHz, CDCl$_3$) δ −109.3; IR (ATR) vmax/cm$^{-1}$ 3238m, 3090w, 2967w, 2111w, 1710s, 1564m, 1501m, 1440m, 1308s, 1212s, 766s; MS (ASAP) m/z=179.0 [M+H]$^+$; HRMS (ASAP) calcd. for $C_{10}H_8O_2F$ [M+H]$^+$: 179.0508, found 179.0495.

1.1.5 Synthesis of Methyl 5-bromopyridine-2-carboxylate, 8

Figure 1E:
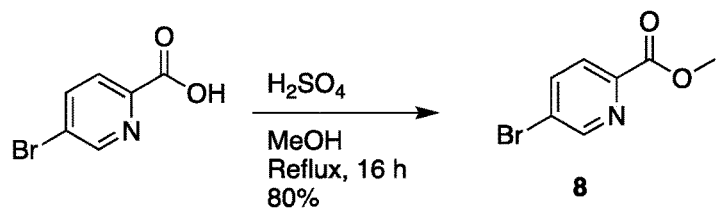
Figure 1F:
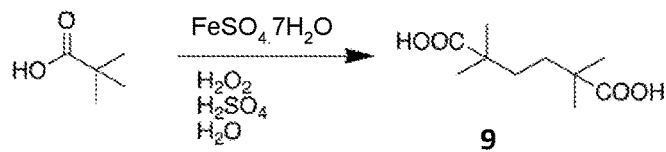
Figure 1G:
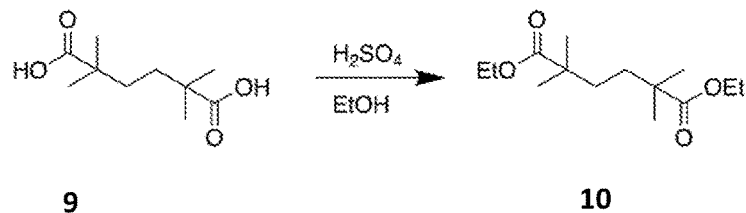
Figure 1H:
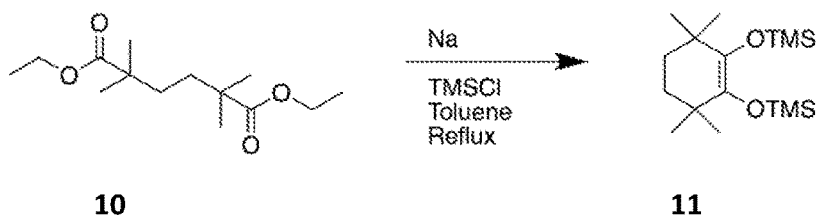
Figure 1I:
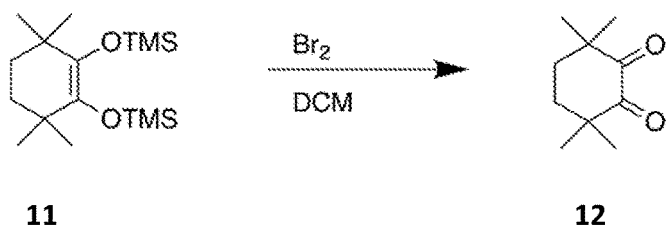
Figure 1J:
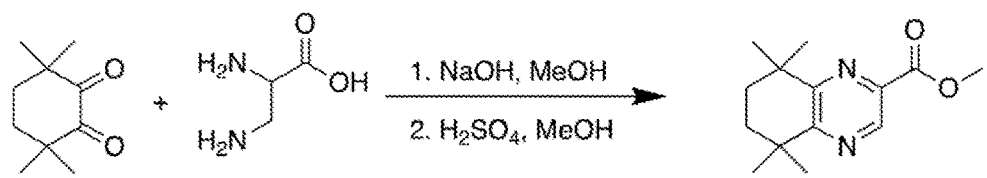
Figure 1K:
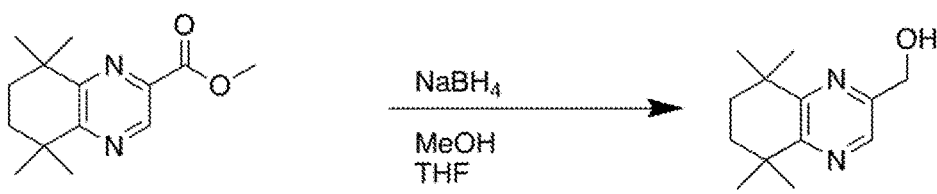
Figure 1L:
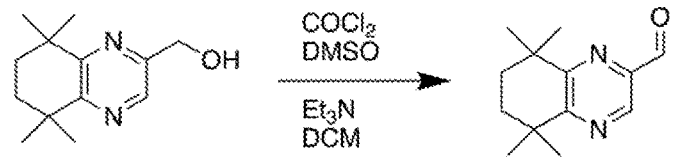

The synthesis of methyl 5-bromopyridine-2-carboxylate (8) is illustrated in FIG. 1(e). 5-Bromopyridine-2-carboxylic acid (20.0 g, 99.0 mmol) was suspended in MeOH (150 ml), whereupon conc. $H_2SO_4$ (5 mL) was carefully added and the resultant solution was stirred at reflux for 6 h. The solution was cooled, diluted with EtOAc, washed with $H_2O$ and brine (50 mL), dried ($MgSO_4$) and evaporated to give a crude colourless solid. This was distilled in vacuo using a Kugelrohr (200° C., 7.4 Torr), and the resultant white solid was further recrystallised from heptane/MeOH (10:1) to give compound 8 as a white solid (17.21 g, 80%): $^1$H NMR (700 MHz, CDCl$_3$) δ 3.90 (s, 4H), 7.86 7.93 (m, 3H), 8.68 (d, J=2.0 Hz, 1H); $^{13}$C NMR (176 MHz, CDCl$_3$) δ 52.8, 124.8, 126.0, 139.5, 146.0, 150.7, 164.7; $v_{max}$/cm$^{-1}$ 3059w, 3008w, 2957w, 1710s, 1571w, 1558w, 1436m, 1305s, 1131s, 696s; MS (ASAP): m/z=216.0 [M+H]$^+$; HRMS (ASAP) calcd. for C$_{10}$H$_9$NOI [M+H]$^+$: 215.9660, found: 215.9664 (Tung et al., Eur. J. Med. Chem. 2017, 126, 1011-1020).

1.1.6 Synthesis of 2,2,5,5-Tetramethylhexanedioic acid, 9

The synthesis of 2,2,5,5-Tetramethylhexanedioic acid (9) is illustrated in FIG. 1(*f*). To a 2 L three-neck flask equipped with mechanical stirrer was added H$_2$O (600 mL), conc. H$_2$SO$_4$ (7.5 mL), then pivalic acid (51.0 g, 500 mmol), and the resultant slurry was cooled to 0° C. Over 15 mins, H$_2$O$_2$ (30%, 43 mL) and a solution of FeSO$_4$.7H$_2$O (139.0 g, 500 mmol) in H$_2$O (288 mL) and conc. H$_2$SO$_4$ (27.5 mL) were added dropwise, with vigorous stirring. After completion of the addition, the suspension was stirred for a further 15 mins, before the solution was concentrated to ca. 250 mL. The precipitated solids were filtered, then dried further under vacuum using a rotary evaporator to give a crude residue. This was recrystallised from AcOH to give 9 as a colourless crystalline solid (3.39 g, 3%): $^1$H NMR (400 MHz, DMSO-d$_6$) δ 1.06 (s, 12H), 1.37 (s, 4H), 12.05 (s, 2H).

1.1.7 Synthesis of 1,6-Diethyl 2,2,5,5-tetramethylhexanedioate, 10

The synthesis of 1,6-Diethyl 2,2,5,5-tetramethylhexanedioate (10) is illustrated in FIG. 1(*g*). To a solution of 9 (3.39 g, 16.76 mmol) in EtOH (40 mL) was added conc. H$_2$SO$_4$ (2 mL), and the resultant suspension was stirred at reflux for 16 h. The solution was cooled, and the solvent evaporated to a give crude residue which was dissolved in EtOAc. The organics were washed with sat. NaHCO$_3$, H$_2$O and brine, dried (MgSO$_4$) and evaporated to give a crude oil (3.8 g). This was purified by SiO$_2$ chromatography (95:5, heptane/EtOAc) to give 10 as a colourless oil (3.41 g, 79%): $^1$H NMR (700 MHz, CDCl$_3$) δ 1.14 (s, 11H), 1.24 (t, J=7.1 Hz, 6H), 4.11 (q, J=7.1 Hz, 4H); $^{13}$C NMR (176 MHz, CDCl$_3$) δ 14.2, 25.0, 35.5, 41.8, 60.2, 177.7; IR (ATR) $v_{max}$/cm$^{-1}$ 2978m, 2934w, 2880w, 1726s, 1475m, 1308m, 1176s, 1110m, 771w; MS(ES): m/z=259.5 [M+H]$^+$.

1.1.8 Synthesis of Trimethyl({3,3,6,6-tetramethyl-2-[(trimethylsilyl)oxy]cyclohex-1-en-1-yl}oxy)silane, 11

The synthesis of Trimethyl({3,3,6,6-tetramethyl-2-[(trimethylsilypoxy]cyclohex-1-en-1-yl}oxy)silane, 11 is illustrated in FIG. 1(*h*). To anhydrous toluene (50 mL) was added sodium (1.20 g, 52.1 mmol) under N$_2$, and the resultant mixture was heated to reflux until the sodium melted. The flask was then removed from the heat, and then 10 (2.69 g, 10.41 mmol) and chlorotrimethylsilane (6.72 mL, 53.0 mmol) were added and the resultant suspension was then stirred at reflux overnight. The purple suspension was then cooled, and filtered under a flow of N$_2$, washing with toluene, then tetrahydrofuran (THF). The filtrate was then evaporated to give a crude light yellow oil (3.2 g), which was purified by Kugelrohr distillation (120° C., 3.6 Torr) to give 11 as a clear oil (2.64 g, 81%): $^1$H NMR (400 MHz, CDCl$_3$) δ 0.19 (s, 18H), 1.03 (s, 12H), 1.44 (s, 4H). All other data matched the literature (Kikuchi et al. J. Med. Chem. 2000; 43: pp. 409-419).

1.1.9 Synthesis of 3,3,6,6-tetramethylcyclohexane-1,2-dione, 12

The synthesis of 3,3,6,6-tetramethylcyclohexane-1,2-dione is illustrated in FIG. 1(*i*). To a solution of 11 (2.6 g, 8.2 mmol) in dichloromethane (DCM) was added bromine (0.42 mL, 8.2 mmol) dropwise over 5 mins. The resultant yellow solution was stirred at RT for 1 h, before being diluted with DCM, and treated with sat. Na$_2$S$_2$O$_3$, then washed with H$_2$O, dried (MgSO$_4$) and evaporated to give a crude yellow solid (1.5 g). This was purified by recrystallisation from heptane to give 12 as a yellow crystalline solid (1.07 g, 78%): $^1$H NMR (700 MHz, CDCl$_3$) δ 1.14 (s, 4H), 1.85 (s, 12H); $^{13}$C NMR (176 MHz, CDCl$_3$) δ 22.9, 34.7, 48.6, 207.3; IR (ATR) $v_{max}$/cm$^{-1}$ 2973m, 2940w, 2870w, 1706s, 1599w, 1459m, 1372m, 1102m, 931m; MS(ES): m/z=169.3 [M+H]$^+$. All other data matched the literature. (Kikuchi et al. J. Med. Chem. 2000; 43: pp. 409-419).

1.1.10 Synthesis of methyl 5,5,8,8-tetramethyl-5,6,7,8-tetrahydroquinoxaline-2-carboxylate, 13

The synthesis of methyl 5,5,8,8-tetramethyl-5,6,7,8-tetrahydroquinoxaline-2-carboxylate, 13 is illustrated in FIG. 1(*j*). 12 (0.80 g, 4.76 mmol) and DL-2,3-diaminopropionic acid hydrochloride (0.67 g, 4.76 mmol) were combined in MeOH (30 mL). NaOH (0.76 g, 19.04 mmol) was added and the resultant mixture was stirred at reflux for 24 h. The solution was then cooled to 0° C., H$_2$SO$_4$ carefully added, and the solution was stirred at reflux for a further 6 h. The solution was cooled, and the solvent evaporated to give a crude residue which was dissolved with EtOAc, washed with sat. NaHCO$_3$, H$_2$O and brine, dried (MgSO$_4$) and evaporated to give a crude yellow oil (0.9 g). This was purified by SiO$_2$ chromatography (95:5, heptane/EtOAc) to give 13 as a colourless oil (0.633 g, 54%): $^1$H NMR (400 MHz, CDCl$_3$) δ 1.33 & 1.36 (s, 12H), 1.81 (s, 4H), 3.98 (s, 3H), 9.00 (s, 1H). All other data matched the literature (Kikuchi et al. J. Med. Chem. 2000; 43: pp. 409-419).

1.1.11 Synthesis of (5,5,8,8-Tetramethyl-5,6,7,8-tetrahydroquinoxalin-2-yl)methanol, 14

The synthesis of (5,5,8,8-Tetramethyl-5,6,7,8-tetrahydroquinoxalin-2-yl)methanol, 14 is illustrated in FIG. 1(*k*). To a solution of 13 (5.09 g, 20.5 mmol) in THF (80 mL) was added NaBH$_4$ (2.33 g, 61.5 mmol). The solution was then heated to reflux, whereupon MeOH (16 mL) was slowly added over 1 h. The resultant solution was then stirred at reflux overnight. The solution was cooled, quenched with 1 M HCl, and the solvent then evaporated. The residue was dissolved in DCM, washed with water, dried (MgSO$_4$) and evaporated to give a crude yellow oil (4 g). This was purified by SiO$_2$ chromatography (8:2, heptane/EtOAc, as eluent) to give 14 as a colourless oil (3.96 g, 88%): $^1$H NMR (400 MHz, CDCl$_3$) δ 1.33 & 1.36 (s, 12H), 1.80 (s, 4H), 3.50 (br, 1H), 4.75 (s, 2H), 8.32 (s, 1H); all other data matched the literature (Kikuchi et al. J. Med. Chem. 2000; 43: pp. 409-419).

1.1.12 Synthesis of 5,5,8,8-Tetramethyl-5,6,7,8-tetrahydroquinoxaline-2-carbaldehyde, 15

The synthesis of 5,5,8,8-Tetramethyl-5,6,7,8-tetrahydroquinoxaline-2-carbaldehyde, 15 is illustrated in FIG. 1(*l*).

Oxalyl chloride (2.28 mL, 26.96 mmol) was added to anhydrous DCM (100 mL) under $N_2$. The resultant solution was cooled to −78° C., whereupon DMSO (3.83 mL, 53.92 mmol) was added dropwise so as to maintain the temperature below −60° C. The solution was stirred for 15 mins before 14, as a solution in anhydrous DCM (3.96 g, 17.97 mmol, in 20 mL) was added dropwise so as to main the temperature below −60° C. The solution was stirred for a further 15 mins before $Et_3N$ (18.03 mL, 129.38 mmol) was added. The solution was then stirred for 10 mins, before being allowed to reach room temperature (RT) over 30 mins. $H_2O$ was added, and the resultant mixture was diluted with DCM, washed with $H_2O$, dried ($MgSO_4$) and evaporated to give a crude oil (4 g). This was purified by dry column vacuum chromatography (DCVC) (heptane to 9:1, heptane/EtOAc) to give 15 as a colourless oil that slowly crystallises (3.39 g, 86%): $^1H$ NMR (700 MHz, $CDCl_3$) δ 1.35 & 1.37 (s, 12H), 1.83 (s, 4H), 8.90 (s, 1H), 10.08 (s, 1H); $^{13}C$ NMR (176 MHz, $CDCl_3$) δ 29.7, 29.7, 33.8, 33.8, 37.4, 37.9, 139.8, 144.2, 159.0, 163.7, 193.4; IR (ATR) $v_{max}/cm^{-1}$ 2979m, 2964m, 2928m, 2862m, 2823w, 1707s, 1553m, 1457m, 1126s, 1078s, 737s; MS(ES): m/z=219.3 $[M+H]^+$; HRMS (ES) calcd. for $C_{13}H_{19}ON_2$ $[M+H]^+$: 216.1497, found 216.1503.

1.1.13 Synthesis of Dimethyl 1-diazo-2-oxopropylphosphonate, 16

Figure 1M:
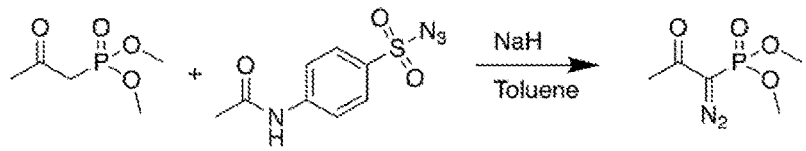

The synthesis of Dimethyl 1-diazo-2-oxopropylphosphonate, 16 is illustrated in FIG. 1(m). To a solution of dimethyl 2-oxopropylphosphonate (4.49 mL, 32.5 mmol) in anhydrous toluene (30 mL) at 0° C. was added NaH (60% dispersion in mineral oil, 1.20 g, 30.00 mmol) portionwise with vigorous stirring. After gas evolution had ceased 4-acetamidobenzenesulfonyl azide (7.21 g, 30.0 mmol), as a solution in anhydrous THF (10 mL), was added dropwise. The resultant suspension was stirred at RT for 16 h, whereupon heptane was added, and the suspension was filtered through Celite®, and rinsed with MTBE. The organic extracts were then evaporated to give a crude oil (5 g), which was purified by $SiO_2$ chromatography (1:1, heptane/EtOAc) to give dimethyl 1-diazo-2-oxopropylphosphonate as a light yellow oil (3.14 g, 54%): $^1H$ NMR (400 MHz, $CDCl_3$) δ 2.24 (s, 3H), 3.82 (d, J=11.9 Hz, 6H), all other data matched the literature (Pietruszka et al. Synthesis, 2006, pp. 4266-4268).

1.1.14 2-Ethynyl-5,5,8,8-tetramethyl-5,6,7,8-tetrahydroquinoxaline, 17

Figure 1N:
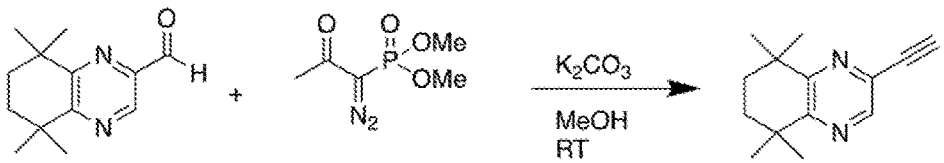

The synthesis of 2-Ethynyl-5,5,8,8-tetramethyl-5,6,7,8-tetrahydroquinoxaline, 17 is illustrated in FIG. 1(n). To a solution of 15 (1.18 g, 5.40 mmol) in anhydrous MeOH (50 mL) under $N_2$ was added $K_2CO_3$ (1.49 g, 10.80 mmol) and dimethyl-1-diazo-2-oxopropylphosphonate (0.98 mL, 6.48 mmol), and the resultant suspension was stirred at RT for 16 h. The solution was diluted with EtOAc, washed with 5% $NaHCO_3$, $H_2O$ and brine, dried ($MgSO_4$) and evaporated to give a crude orange oil (0.4 g). This was purified by $SiO_2$ chromatography (95:5, heptane/EtOAc, as eluent) to give 17 as a colourless oil that slowly crystallised (0.84 g, 73%): $^1H$ NMR (700 MHz, $CDCl_3$) δ 1.30 & 1.31 (s, 12H), 1.77 (s, 4H), 3.22 (s, 1H), 8.45 (s, 1H); $^{13}C$ NMR (176 MHz, $CDCl_3$) δ 29.6, 29.7, 33.8, 34.0, 37.2, 37.3, 79.0, 81.0, 135.4, 144.5, 158.1, 158.6; IR (ATR) $v_{max}/cm^{-1}$ 3279s, 2986w, 2945m, 2917m, 2863w, 2110w, 1519w, 1470m, 1459m, 1274m, 1078s, 674s; MS(ES): m/z=215.3 $[M+H]^+$; HRMS (ES) calcd. for $C_{14}H_{19}N_2$ $[M+H]^+$: 215.1548, found 215.1548.

1.2 Synthesis of 3-Fluoro-4-[2-(5,5,8,8-tetramethyl-5,6,7,8-tetrahydronaphthalen-2-yl)ethynyl]benzoic acid, DC526

Figure 2:
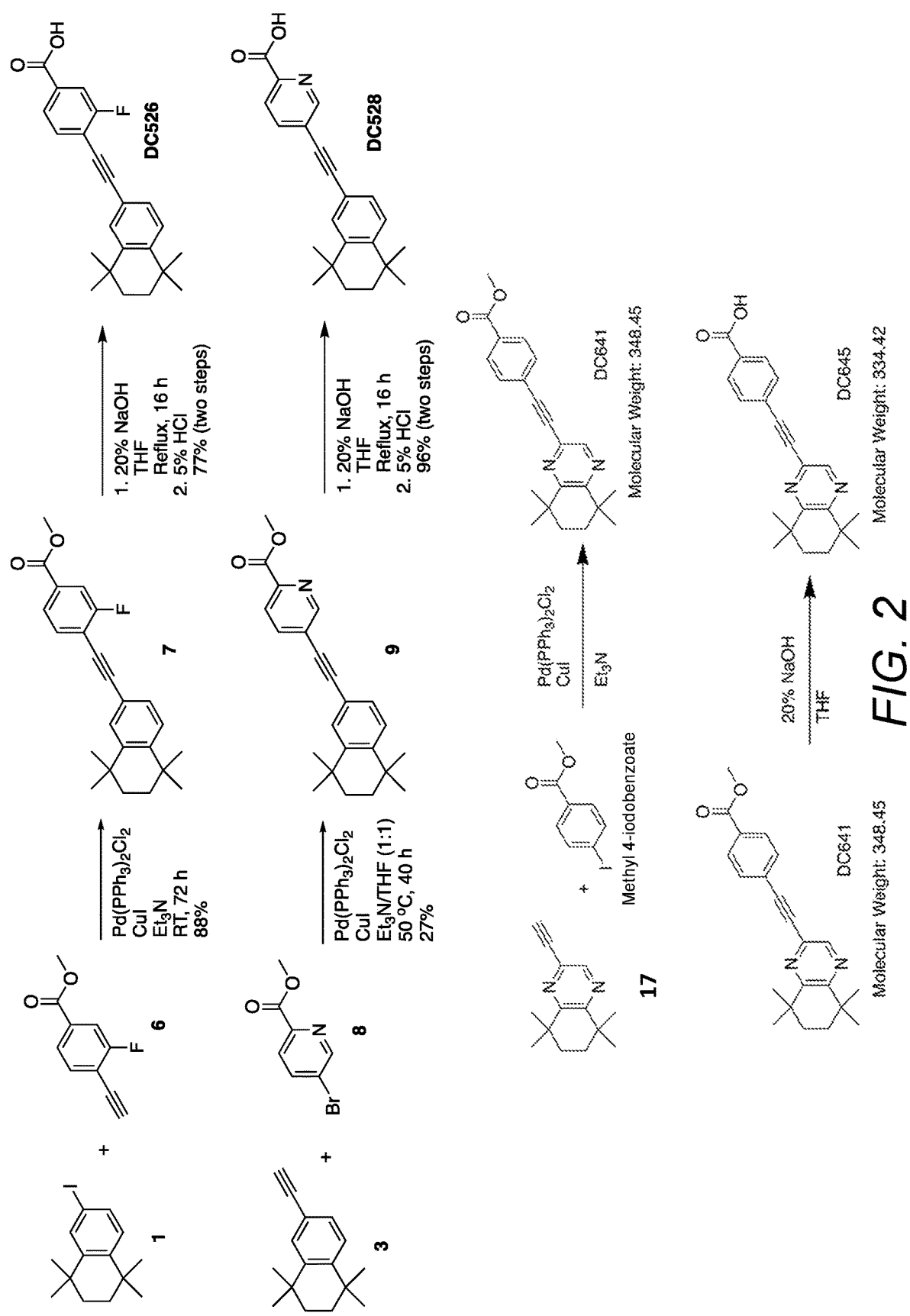
FIG. 2 illustrates the synthesis of exemplary retinoid compounds DC526, DC528, DC641 and DC645.

The synthesis of exemplary compound DC526 is illustrated in FIG. 2a.

$Et_3N$ (80 mL) was degassed by sparging with $N_2$ for 1 hour. Compound 1 (0.80 g, 2.55 mmol), compound 6 (0.54 g, 3.05 mmol), $Pd(PPh_3)_2Cl_2$ (179 mg, 0.255 mmol) and CuI (49 mg, 0.255 mmol) were then added under $N_2$ and the resultant suspension was stirred at room temperature for 72 hours. The suspension was diluted with MTBE and passed through Celite®/$SiO_2$ and the extracts were evaporated to a give a crude solid (1.1 g). This was purified by dry column vacuum chromatography (100% heptane, to 95:5, heptane/EtOAc) to give compound 7 as a colourless oil which slowly crystallised (0.82 g, 88%), which was carried directly to the next step. Compound 7 (0.80 g, 2.20 mmol) was dissolved in THF (40 mL), 20% NaOH (3 mL) added, and the resultant solution was stirred at reflux for 16 hours. The mixture was cooled, acidified to pH 1 with 5% HCl, extracted with EtOAc, washed with $H_2O$ and brine, dried ($MgSO_4$) and evaporated to give a crude white solid which was recrystallised from Acetonitrile (MeCN) to give DC526 as a colourless crystalline solid (0.60 g, 77%): $^1H$ NMR (600 MHz, DMSO-$d_6$) 1.24 & 1.26 (s, 12H), 1.64 (s, 4H), 7.32 (dd, J=8.1, 1.8 Hz, 1H), 7.40 (d, J=8.2 Hz, 1H), 7.53 (d, J=1.8 Hz, 1H), 7.70 7.78 (m, 2H), 7.80 (dd, J=7.9, 1.6 Hz, 1H), 13.44 (br, 1H); $^{13}C$ NMR (151 MHz, DMSO-$d_6$) δ 31.3, 31.4, 33.9, 34.1, 34.2, 34.3, 81.0, 97.4 (d, J=3.1 Hz), 115.2, 115.3 (d, J=15.8 Hz), 116.0 (d, J=22.3 Hz), 118.5, 125.4 (d, J=3.4 Hz), 127.1, 128.7, 129.6, 132.7 (d, J=7.1 Hz), 133.6, 145.2, 146.5, 161.4 (d, J=250.3 Hz), 165.7 (d, J=2.5 Hz); $^{19}F$ NMR (376 MHz, DMSO-$d_6$) δ −110.0; IR (ATR) $v_{max}/cm^{-1}$ 2967m, 2928m, 2857m, 2210w, 1686s, 1617m, 1566m, 1421m, 1307m, 1218m, 834s, 764m; MS(ASAP): m/z=351.2 $[M+H]^+$; HRMS (ASAP) calcd. for $C_{23}H_{24}O_2F$ $[M+H]^+$: 351.1760, found 351.1766.

1.3 Synthesis of 5-[2-(5,5,8,8-tetramethyl-5,6,7,8-tetrahydronaphthalen-2-yl)ethynyl]pyridine-2-carboxylic acid, DC528

The synthesis of exemplary compound DC528 is illustrated in FIG. 2b $Et_3N$/THF (1:1, 120 mL) was degassed by sparging with $N_2$ for 1 h. $Pd(PPh_3)_2Cl_2$ (0.265 g, 0.38 mmol), CuI (0.072 g, 0.38 mmol), compound 3 (0.8 g, 4.80 mmol) and compound 8 (0.98 g, 4.52 mmol) were added under $N_2$ and the resultant solution was stirred at 50° C. for 40 h. The solution was diluted with heptane, and eluted through a Celite®/$SiO_2$ plug with heptane. The organics were then washed with sat. $NH_4Cl$, $H_2O$ and brine, dried ($MgSO_4$) and evaporated to give a crude brown solid (1.9 g). This was purified by dry column vacuum chromatography (100% heptane to 8:2, heptane/EtOAc), to give compound 9 as a white solid (0.36 g, 27%), which was carried directly to the next step: $^1H$ NMR (400 MHz, $CDCl_3$) δ 1.29 (d, J=7.9 Hz, 12H), 1.69 (s, 4H), 4.02 (s, 3H), 7.31 (d, J=1.1 Hz, 2H), 7.51 (s, 1H), 7.94 (dd, J=8.1, 2.1 Hz, 1H), 8.12 (dd, J=8.1, 0.9 Hz, 1H), 8.85 (dd, J=2.1, 0.9 Hz, 1H). Compound 9 (0.33 g, 0.95 mmol) was dissolved in THF (30 mL), 20% NaOH (3 mL) added, and the resultant solution was stirred at reflux for 16 h. The mixture was cooled, acidified to pH 1 with 5% HCl, extracted with EtOAc, washed with $H_2O$ and brine, dried (MgSO$_4$) and evaporated to give a crude white solid. This was recrystallised from MeCN to give DC528 as a colourless crystalline solid (0.30 g, 96%): $^1$H NMR (700 MHz, DMSO-d$_6$) δ 1.25 & 1.27 (s, 12H), 1.65 (s, 4H), 7.35 (dd, J=8.1, 1.8 Hz, 1H), 7.41 (d, J=8.1 Hz, 1H), 7.57 (d, J=1.8 Hz, 1H), 8.06 (dd, J=8.1, 0.9 Hz, 1H), 8.12 (dd, J=8.1, 2.1 Hz, 1H), 8.85 (dd, J=2.1, 0.9 Hz, 1H), 13.35 (s, 1H); $^{13}$C NMR (176 MHz, DMSO-d$_6$) δ 31.3, 31.4, 33.9, 34.1, 34.2, 34.3, 39.5, 84.8, 95.4, 118.4, 122.7, 124.3, 127.1, 128.7, 129.8, 139.5, 145.2, 146.4, 146.9, 151.3, 165.6; IR (ATR) $v_{max}$/cm$^{-1}$ 3283br, 2955m, 2920m, 2856m, 2208m, 1752s, 1586m, 1336s, 1247m, 1017m, 833m; MS(ES): m/z=334.2 [M+H]$^+$; HRMS (ES) calcd. for C$_{22}$H$_{24}$NO$_2$ [M+H]$^+$: 334.1807, found 334.1808.

1.4 Synthesis of Methyl 4-[2-(5,5,8,8-tetramethyl-5,6,7,8-tetrahydroquinoxalin-2-yl)ethynyl]benzoate, DC641

The synthesis of exemplary compound DC641 is illustrated in FIG. 2c. Et$_3$N (20 mL) was degassed by sparging with Ar for 1 h. Methyl 4-iodobenzoate (0.31 g, 1.20 mmol), DC640 (0.30 g, 1.40 mmol), Pd(PPh$_3$)$_2$Cl$_2$ (83 mg, 0.12 mmol) and CuI (22 mg, 0.12 mmol) were then added under Ar and the resultant suspension was stirred at RT for 16 h. The suspension was diluted with MTBE and passed through Celite®/SiO$_2$ and the extracts were evaporated to a give a crude solid (0.5 g). This was purified by dry column vacuum chromatography (100% heptane to 85:15, heptane/EtOAc) to give an off-white solid which was subsequently recrystallised from MeOH to give DC641 as a colourless crystalline solid (0.29 g, 71%), which was carried directly to the next step: $^1$H NMR (400 MHz, CDCl$_3$) δ 1.33 & 1.35 (s, 12H), 1.81 (s, 4H), 3.94 (s, 3H), 7.64 7.71 (m, 2H), 8.01-8.08 (m, 2H), 8.52 (s, 1H).

1.5 Synthesis of 4-[2-(5,5,8,8-Tetramethyl-5,6,7,8-tetrahydroquinoxalin-2-yl)ethynyl]benzoic acid, DC645

The synthesis of exemplary compound DC645 is illustrated in FIG. 2d. DC641 (0.28 g, 0.8 mmol) was dissolved in THF (20 mL), 20% NaOH (2 mL) added, and the resultant solution was stirred at reflux for 16 h. The mixture was cooled, acidified to pH 1 with 5% HCl, extracted with EtOAc, washed with H$_2$O and brine, dried (MgSO$_4$) and evaporated to give a crude white solid which was recrystalised from MeCN to give DC645 as a colourless crystalline solid (0.24 g, 89%): $^1$H NMR (700 MHz, DMSO-d$_6$) δ 1.29 (s, 12H), 1.78 (s, 4H), 7.73 7.79 (m, 2H), 7.98 8.02 (m, 2H), 8.68 (s, 1H), 13.24 (br, 1H); $^{13}$C NMR (176 MHz, DMSO-d$_6$) δ 29.4, 29.4, 33.1, 33.2, 37.0, 37.1, 88.9, 89.8, 125.2, 129.6, 131.3, 131.9, 135.2, 144.4, 157.6, 158.0, 166.5; IR (ATR) $v_{max}$/cm$^{-1}$ 2961w, 2925w, 2958w, 2223w, 1683s, 1606m, 1558w, 1428m, 1282s, 862s, 769m; MS(ASAP): m/z=334.2 [M]$^+$; HRMS (ASAP) calcd. for C$_{21}$H$_{22}$N$_2$O$_2$ [M]$^+$: 334.1681, found 334.1686.

EXAMPLE 2: BIOLOGICAL EVALUATION

2.1 Genomic Activity of Synthetic Retinoids

The genomic activity of synthetic retinoids was evaluated by determining their efficiency of inducing transcription using the X-Gal Assay. The X-Gal Assay utilizes Sil-15 reporter cells in which the transcription of the LacZ gene is under control of a promoter linked to a retinoic acid response element (RARE). After treatment of the reporter cells with retinoids, the ability of the compounds to induce transcription can be attained by monitoring and quantifying the activity of β-galactosidase produced by the reporter cells.

Sil-15 cells were plated at 100,000 cells per well in 96-well plates coated in 0.1% gelatin. The following day, serial dilutions of retinoid ligands, prepared in Dulbecco's Modified Eagle's Medium (DMEM) containing 10% foetal calf serum (FCS) were added at concentrations from 10$^{-6}$ M to 10$^{-14}$ M and the plates were incubated overnight. All concentrations for the ATRA standard curve and the other retinoid ligands were tested in triplicate.

The next day, the assay plates were washed twice with phosphate buffered saline (PBS), fixed with 100 μl per well of 1% glutaraldehyde and 1 mM MgCl$_2$ in PBS for 15 minutes and washed twice with PBS. β-galactosidase activity was detected by the addition of 100 μl of freshly-prepared 0.2% X-Gal in 1 mM MgCl$_2$, 3.3 mM potassium ferricyanide and 3.3 mM potassium ferrocyanide in PBS per well. Plates were incubated for 6 hours at 37° C. in 5% CO$_2$ and colour change was detected by reading the plates at 650 nm on an Emax Precision Microplate Reader (Molecular Devices).

Figure 3:
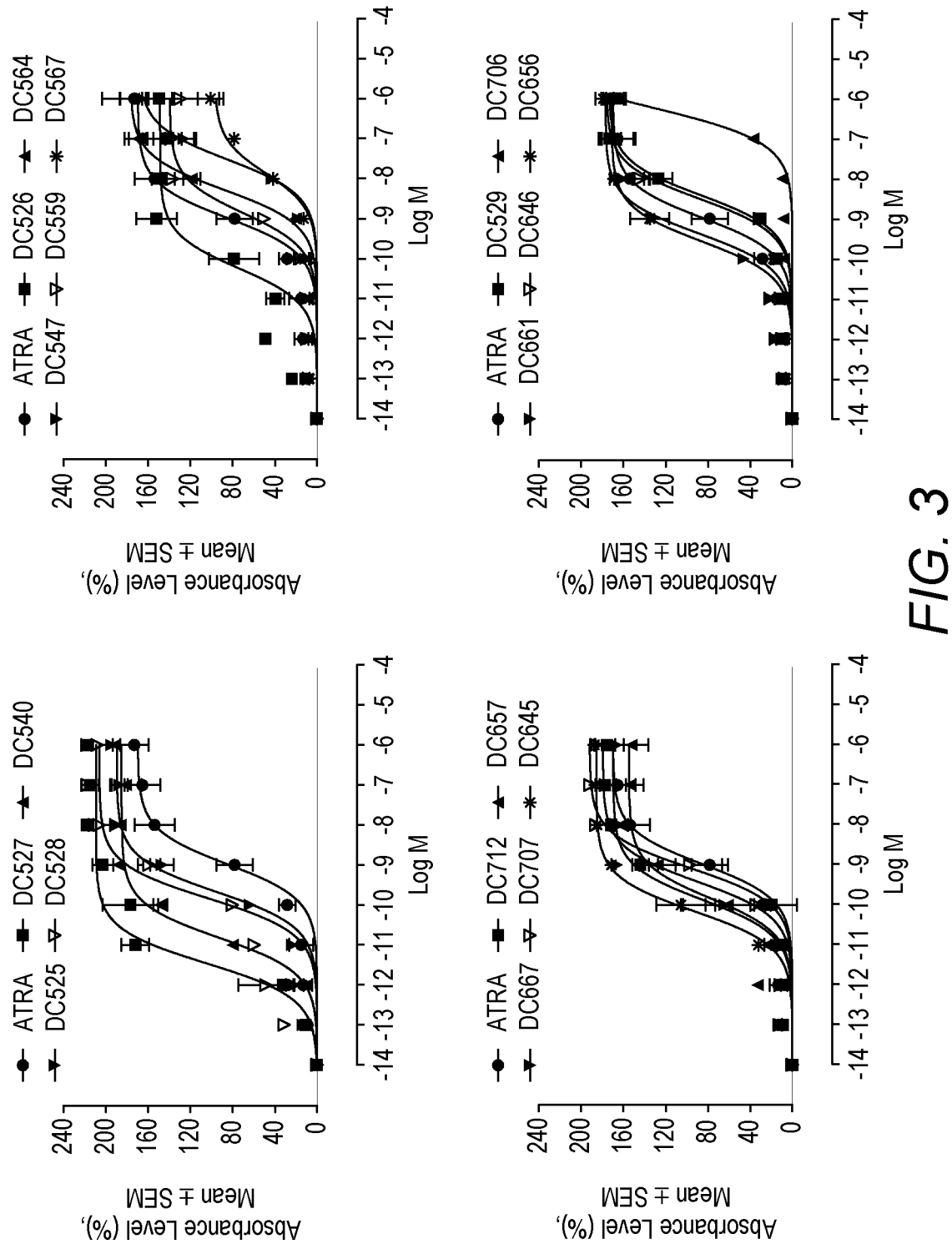
FIG. 3 illustrates the genomic activity of retinoids as indicated by use of the X-Gal assay.

The resulting data, as shown in Table 1 and illustrated in FIG. 3, demonstrates that several of the synthetic retinoids displayed greater genomic activity than that of the endogenous ligand (ATRA) as demonstrated by increased ability to induce transcription in the reporter cells. Notably, DC527, DC540, DC525, DC528, DC526 and DC645 all demonstrated increased genomic activity and potency when compared to retinoic acid (ATRA).

2.2 Non-Genomic Activity of Synthetic Retinoids

The non-genomic activity of synthetic retinoids was evaluated by measuring their ability to induce phosphorylation of ERK1/2 using the AlphaLISA® SureFire® Ultra ERK1/2 kit.

In this assay, SH-SY5Y cells (100,000 cells/well) were plated in 96-well plates and serum-starved in DMEM for 24 hours. Retinoids were tested at concentrations from 10-5 M to 10-11 M and at a final concentration of 0.1% DMSO in the medium. The assay was carried out on the SH-SY5Y cells in serum-free DMEM, cells were stimulated by retinoid for 30 minutes at 37° C.

At the end of the assay, the medium was removed, and cells were lysed in 50 μl of freshly prepared 1× lysis buffer (supplied in the kit). The 96-well plate was agitated on an orbital shaker (SO1, Stuart Scientific) at approximately 350 rpm for 10 minutes at room temperature.

In the meantime, the activation buffer was diluted 25-fold in the reaction buffers. Under green light in a dark room, the acceptor beads were diluted 50-fold in the freshly prepared reaction mix while the donor beads were diluted 50-fold in dilution buffer to obtain two final reaction mixtures.

10 μl of cell lysate was then transferred per well into 384-well white Proxiplates plates (PerkinElmer) and 5 μl of each prepared acceptor and donor reaction mixture was added under green light in a dark room. Plates were wrapped with aluminium foil and incubated at room temperature for at least 3 hours. Readings were taken using an Envision system (PerkinElmer Life Sciences) using the AlphaScreen® settings.

Figure 4:
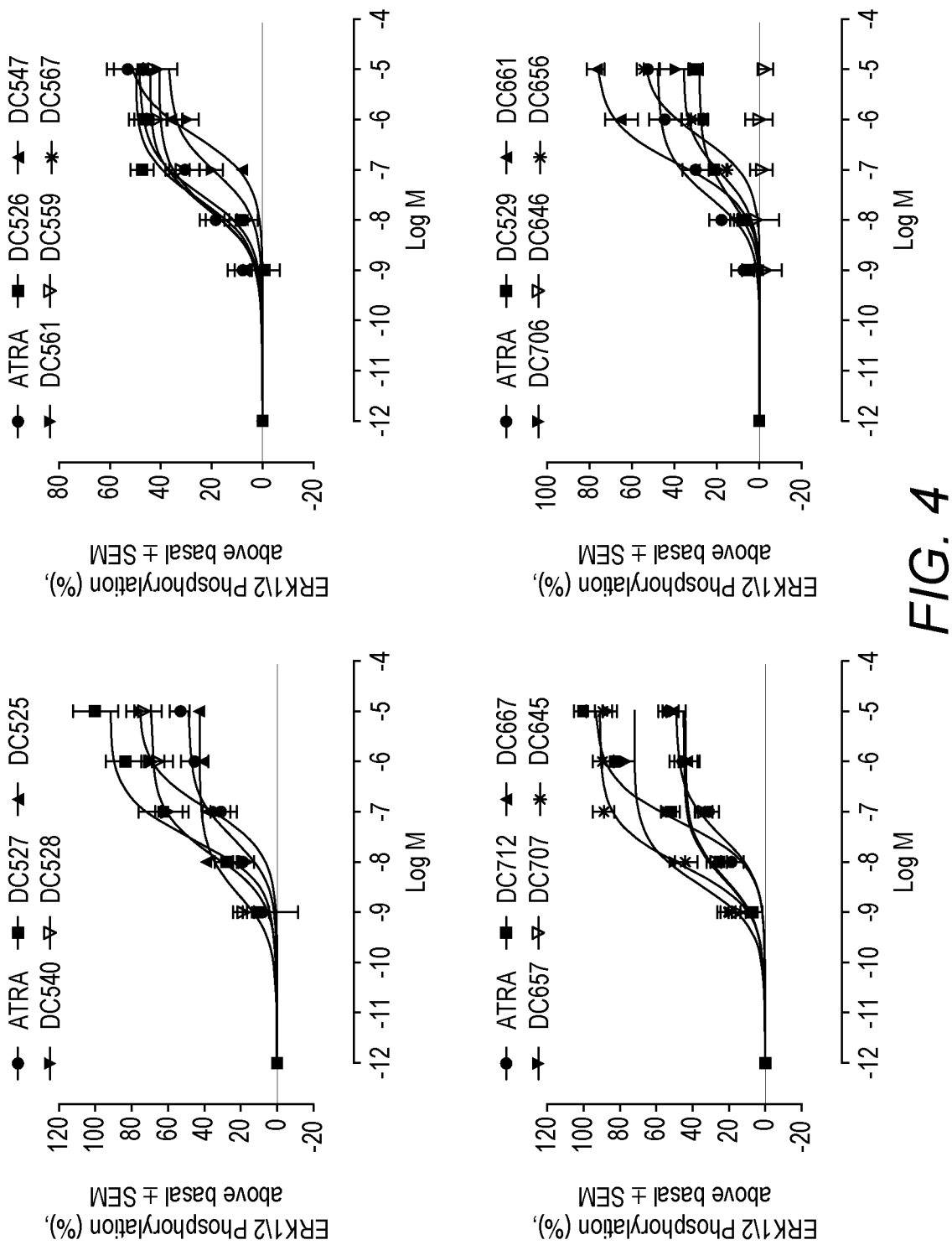
FIG. 4 illustrates the non-genomic activity of retinoids as indicated by their ability to induce phosphorylation of ERK1/2.

The results, shown in Table 1 and illustrated in FIG. 4 demonstrate the ability of retinoids to induce Erk 1/2 phosphorylation in SH-SY5Y cells. Several retinoids were identified having both higher potency and efficacy than retinoic acid such as DC527, DC540, DC528, DC526 and DC645, with DC525 identified as having higher potency.

2.3 Induction of Neurite Outgrowth

SY—SY5Y cells were plated at 10,000 cells/well in 12-well plates containing acid-treated/poly-L-lysine-coated coverslips. After 24 hours, each retinoid was added to the medium at a concentration of 10 nM and the plates were incubated for 5 days. After retinoid treatment, SH-SY5Y cells on coverslips were washed twice in PBS, fixed in 4% paraformaldehyde (PFA) for 20 minutes at room temperature, and washed twice with PBS.

For immunocytochemical staining of neurites, cells on coverslips were washed three times in PBS, and incubated in blocking solution (10% donkey serum and 0.1% triton X-100 in PBS) for 1 hour at room temperature. Cells were then labelled by incubation overnight at 4° C. with β-III tubulin primary antibody (Sigma-Aldrich) diluted 1:1000 in blocking buffer. Following incubation overnight, cells were washed three times with PBS containing 0.1% Triton X-100 solution (PBST) before incubation with anti-mouse monoclonal secondary antibody (1:300 in PBST; Jackson Immunoresearch) for 2 hours at room temperature. Finally, after three washes in PBST and a final wash in PBS, the coverslips were mounted on slides and stored at 4° C.

ImageJ software with the NeuronJ plugin was used to quantify neurite outgrowth on stained cells. For each experiment, 10 different randomly selected images were taken from each cover slip using a Nikon Eclipse E400 fluorescence microscope. Each image was converted into an 8-bit image (necessary for the NeuronJ plugin) and optimised with the brightness and contrast tool in GIMP (GNU Image Manipulation Program). For each image, individual traces were drawn for each clearly-identifiable neurite using the tracing tool in the NeuronJ plugin. Neurite length was measured in pixels and transformed into the corresponding length in μm depending on the magnification used. The average neurite length for each image was calculated by dividing total neurite length by the total number of neurites per image. Ten images per cover slip were measured and the mean calculated for the coverslip overall. Coverslips were in triplicate for each retinoid and concentration.

Figure 5:
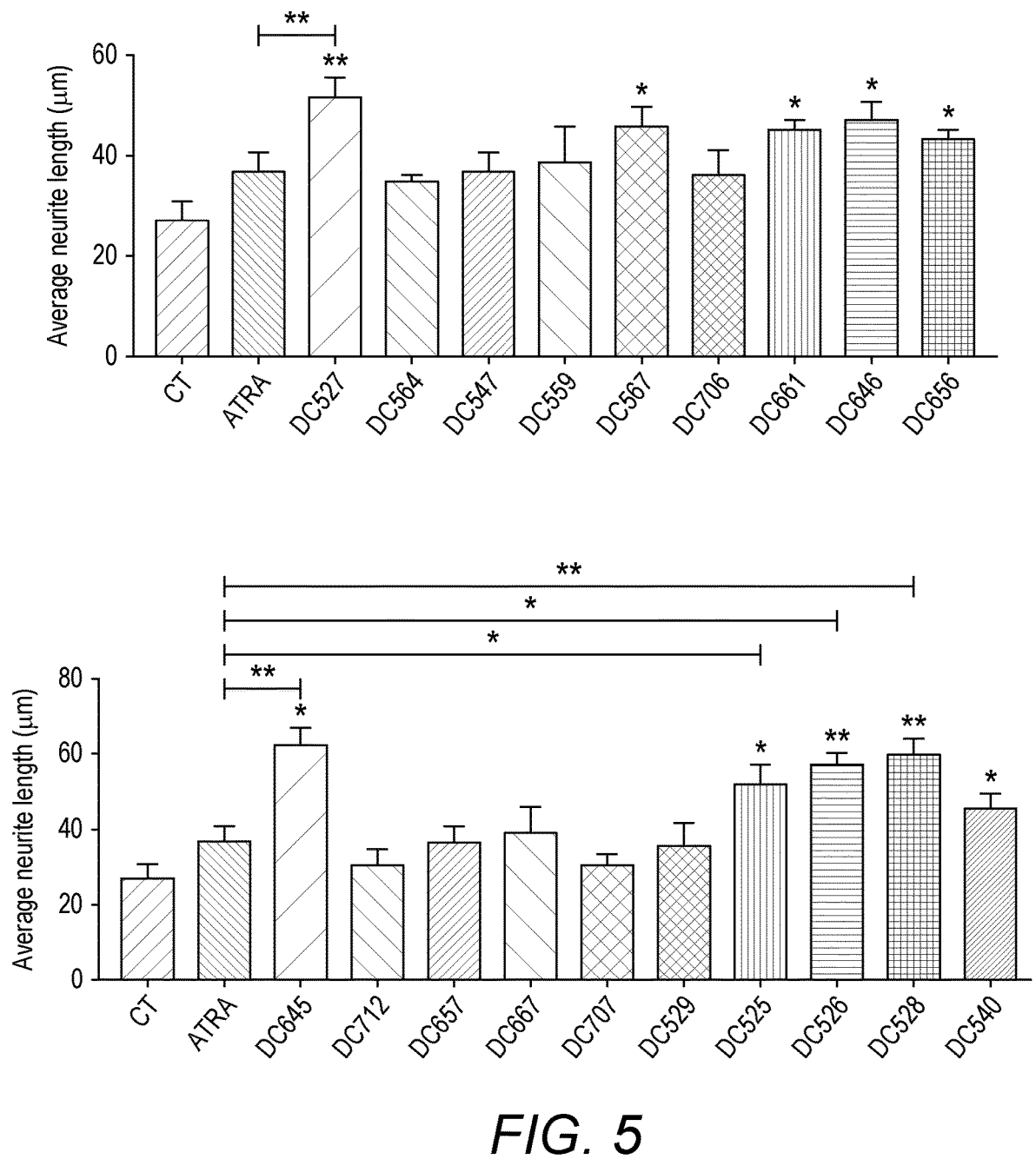
FIG. 5 illustrates average neurite length of differentiated SH-SY5Y cells following treatment with retinoids.
Figure 6:
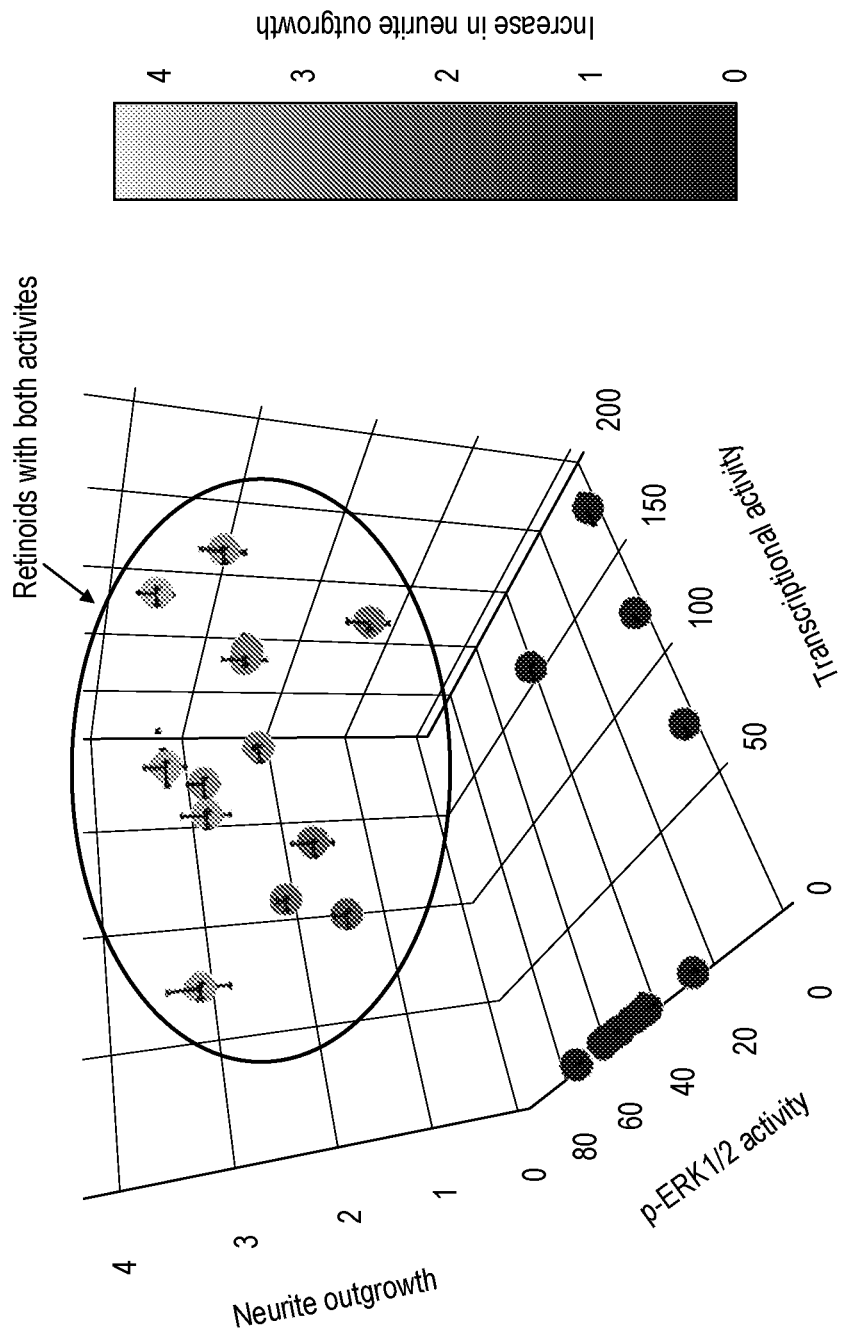
FIG. 6 shows the relationship between the ability of retinoids to induce both genomic activity [(transcriptional activity: $E_{max}$(efficacy)] and non-genomic activity [ERK1/2 activity: $E_{max}$(efficacy)] and the induction of neurite outgrowth (fold increase at 10 μM), with the highlighted retinoids showing both activities.

Data shown in FIG. 5 demonstrates that several of the retinoids showed the ability to induce neurite outgrowth in SY—SY5Y cells. Furthermore, cells treated with several of these compounds (DC527, DC525, DC528, DC526 and DC645) showed a significantly larger average neurite length than cells treated with ATRA.

Table 1 below summarises the genomic (transcriptional activity) and non-genomic activity (p-ERK ½ activity) for the retinoid compounds tested, along with increase in neurite outgrowth, and these results were plotted in FIG. 5. From this figure it is evident that the compounds which showed high efficacy in both the genomic and non-genomic assays demonstrated increased neurite outgrowth induction. This indicates that "dual-potent" compounds, i.e. those which induce both genomic and non-genomic activities, are likely to prove more efficacious in clinical use, allowing this dual assay method to act as a potentially powerful screening tool for new therapeutic compounds.

TABLE 1

Genomic activity, non-genomic activity and neurite outgrowth

| Compound | Genomic Activity (X-Gal RA Based Reporter Assay) | | Non-genomic activity (ERK½ Phosphorylation Assay) | | Neurite Outgrowth |
| --- | --- | --- | --- | --- | --- |
| | Potency ($EC_{50}$) nM (95% CI) | Efficacy ($E_{max}$) (95% CI) | Potency ($EC_{50}$) nM (95% CI) | Efficacy ($E_{max}$) (95% CI) | Fold increase (10 nM) |
| ATRA | 1.044 (83.96 to 1.291) | 170.1 (164.4 to 175.7) | 33.07 (23.76 to 44.85) | 48.55 (46.72 to 50.42) | 1.4 |
| EC23 | 0.1279 (0.08006 to 0.2033) | 169.18 (159.1 to 180.7) | 31.75 (20.21 to 49.83) | 91.93 (86.3 to 100.29) | 2.2 |
| DC527 | 0.003475 (0.002472 to 0.004869) | 209.8 (201.4 to 218.3) | 30.55 (19.47 to 48.53) | 92.51 (85.7 to 99.62) | 1.9 |
| DC540 | 0.01504 (0.01203 to 0.01888) | 185.3 (180.4 to 190.2) | 159.4 (117.7 to 215.5) | 79.73 (75.14 to 84.46) | 1.7 |
| DC525 | 0.2103 (0.1505 to 0.2952) | 190 (181.9 to 198.3) | 2.491 (1.966 to 3.152) | 42.44 (40.92 to 43.98) | 1.9 |
| DC528 | 0.146 (0.06294 to 0.3296) | 206.5 (187.3 to 226.2) | 14.22 (9.415 to 21.28) | 69.15 (65.02 to 73.35) | 2.2 |
| DC526 | 0.05807 (0.02068 to 0.1292) | 149.1 (134.2 to 164) | 26.35 (19.51 to 35.49) | 50.22 (47.4 to 53.09) | 2.1 |
| DC564 | 5.31 (3.966 to 7.03) | 177.1 (168.1 to 186.3) | 18.07 (9.765 to 35.5) | 44.46 (40.82 to 48.35) | 1.3 |
| DC559 | 1.379 (81.11 to 2.297) | 139.8 (127.8 to 151.9) | 15.66 (12.25 to 20.1) | 40.68 (39.24 to 42.15) | 1.4 |
| DC567 | 13.57 (8.721 to 21.17) | 97.21 (89.5 to 105.3) | 18.07 (9.765 to 35.5) | 44.46 (40.82 to 48.35) | 1.6 |
| DC712 | 0.3818 (0.3011 to 0.4824) | 179.7 (173.1 to 186.3) | 6.349 (46.62 to 84.46) | 94 (89.63 to 98.43) | 1.2 |
| DC657 | 0.1463 (0.08618 to 0.2479) | 154.9 (144.4 to 165.5) | 3.496 (2.147 to 5.656) | 72.45 (68.39 to 76.62) | 1.4 |
| DC667 | 0.1336 (0.09097 to 0.1948) | 169.8 (160.5 to 179.2) | 4.849 (2.969 to 7.672) | 44.3 (41.6 to 47.05) | 1.4 |
| DC707 | 0.8256 (0.5211 to 1.266) | 192.2 (179.6 to 205) | 4.323 (2.302 to 7.727) | 44.87 (41.83 to 47.98) | 1.2 |
| DC645 | 0.06965 (0.05443 to 0.08835) | 185.9 (180.2 to 191.6) | 8.538 (6.708 to 10.75) | 91.57 (88.37 to 94.79) | 2.3 |
| DC529 | 3.891 (2.935 to 5.117) | 174 (165.8 to 182.3) | 30.37 (21.26 to 43.1) | 28.85 (27.3 to 30.44) | 1.3 |

TABLE 1-continued

| | Genomic activity, non-genomic activity and neurite outgrowth | | | | |
|---|---|---|---|---|---|
| | Genomic Activity (X-Gal RA Based Reporter Assay) | | Non-genomic activity (ERK½ Phosphorylation Assay) | | Neurite Outgrowth |
| Compound | Potency ($EC_{50}$) nM (95% Cl) | Efficacy ($E_{max}$) (95% Cl) | Potency ($EC_{50}$) nM (95% Cl) | Efficacy ($E_{max}$) (95% Cl) | Fold increase (10 nM) |
| DC706 | 603.2 (409.4 to 1022) | 265.9 (228.8 to 339.2) | 90.8 (58.85 to 138.4) | 36.87 (34.15 to 39.68) | 1.3 |
| DC661 | 0.2701 (0.2064 to 0.3532) | 171.4 (165.3 to 177.5) | 2.004 (1.39 to 2.93) | 53.91 (51.5 to 56.36) | 1.6 |
| DC646 | 3.159 (2.385 to 4.169) | 176.3 (167.8 to 184.9) | 143.5 (117.8 to 174.9) | 77.63 (74.75 to 80.58) | 1.7 |
| DC656 | 0.4274 (0.335 to 0.5427) | 177.2 (170.6 to 183.9) | 501.6 (260.3 to 854.2) | 56.77 (50.45 to 63.47) | 1.6 |

2.4 Regulation of Alzheimer's Disease Related Genes

To examine the influence retinoids may have on the expression of genes involved in Alzheimer's disease, the expression of a group of Alzheimer's-related genes in rat mixed primary neuronal/glial cultures was assessed following retinoid treatment.

Approximately 300,000 rat neuronal/glial cells were treated first with 1 µg/ml lipopolysaccharide (Sigma-Aldrich) for 6 hours to induce inflammation. Following the induction of inflammation, cells were treated with 10 nM retinoids for 24 hours. The retinoids which proved most potent in previous assays were selected for use in these experiments. Following treatment, RNA was extracted from the treated cells for qPCR analysis.

Total RNA was extracted using a Qiagen RNeasy mini kit (CAT # 74104, Qiagen) according to the manufacturer's protocol. Briefly, cell and brain tissue samples were homogenized in 350 µl and 1200 µl of RLT buffer mixed with β-ME (1 ml buffer: 10 µl β-ME ratio) respectively. Then, samples were centrifuged for 3 min at 13,000 rpm. The supernatant was first mixed with 70% ethanol at a 1:1 volume ratio (CAT # E7023, Sigma-Aldrich) before transferring it to a spin column placed in a collection tube. The samples were centrifuged for 1 min at 10,000 rpm to bind RNA to the membrane of the spin column.

For the on-column DNase digestion, the samples in the columns were washed with 350 µl RW1 buffer and centrifuged at 10,000 rpm for 1 min. Then, 80 µl of the DNase mixture (10 µl DNase enzyme with 70 µl RDD buffer; CAT # 79254, Qiagen) was added above each sample. Samples were incubated at room temperature for 15 min before adding 350 µl RW1 buffer. Samples were centrifuged at 10,000 rpm for 1 min.

Afterwards, 500 µl of RPE buffer (mixed with 100% ethanol at 1:4 ratio) was added above the samples. Samples were centrifuged for 1 min at 10,000 rpm (the step was repeated 2 times). The spin columns were centrifuged again at 13,000 rpm for 1 min to dry the membranes. The spin columns were removed from the collection tubes and placed inside another 1.5 ml RNase free collection tubes. The RNA was eluted by adding 30 µl of RNase free water directly to the spin column membrane. The samples were incubated 5 min at room temperature before spinning them for 1 min at 10,000 rpm.

RNA concentration was measured using a NanoDrop™ 2000c spectrophotometer (Thermo Fisher Scientific). The instrument was calibrated using the RNase free water used to elute the RNA as a blank and 2 µl was used of each RNA sample. RNA samples were stored in a −70° C. freezer to minimize RNA degradation.

qPCR reactions were performed using PerfeCTa SYBR Green SuperMix (CAT # 733-1246, VWR). 10 µl of reaction mix was added to each well of a 384-well plate (CAT # 04729749001, Roche) in triplicate. Each reaction contained 2 µl of 4 times diluted cDNA template, 5 µl 2×SYBR green mix and 250 nM primers.

Primers were designed using Primer-BLAST with melting temperatures of about 60° C. Before using them in qPCR, the primers were checked for specificity by PCR and the PCR products were sent for sequencing.

Standard curves (made using 5-fold dilutions of the stock cDNA) and blank controls were run for all sets of primers tested in qPCR. The plates were then sealed and centrifuged briefly to ensure all the reagents were at the base of the wells. The plates were run on a Roche LightCycler 480 that was programmed to hold the plate at 95° C. for 5 min. The qPCR then ran for 45 cycles of 95° C. for 15 seconds (s), 60° C. for 15 s and 72° C. for 15 s. Afterwards, the melting curve was obtained by running the plate at 95° C. for 5 s followed by 58° C. for 1 min.

Results were analysed using the delta delta CT method within the LightCycler 480 1.5 software. The expression of genes of interest was normalized to the appropriate reference gene according to each experiment.

Figure 7:
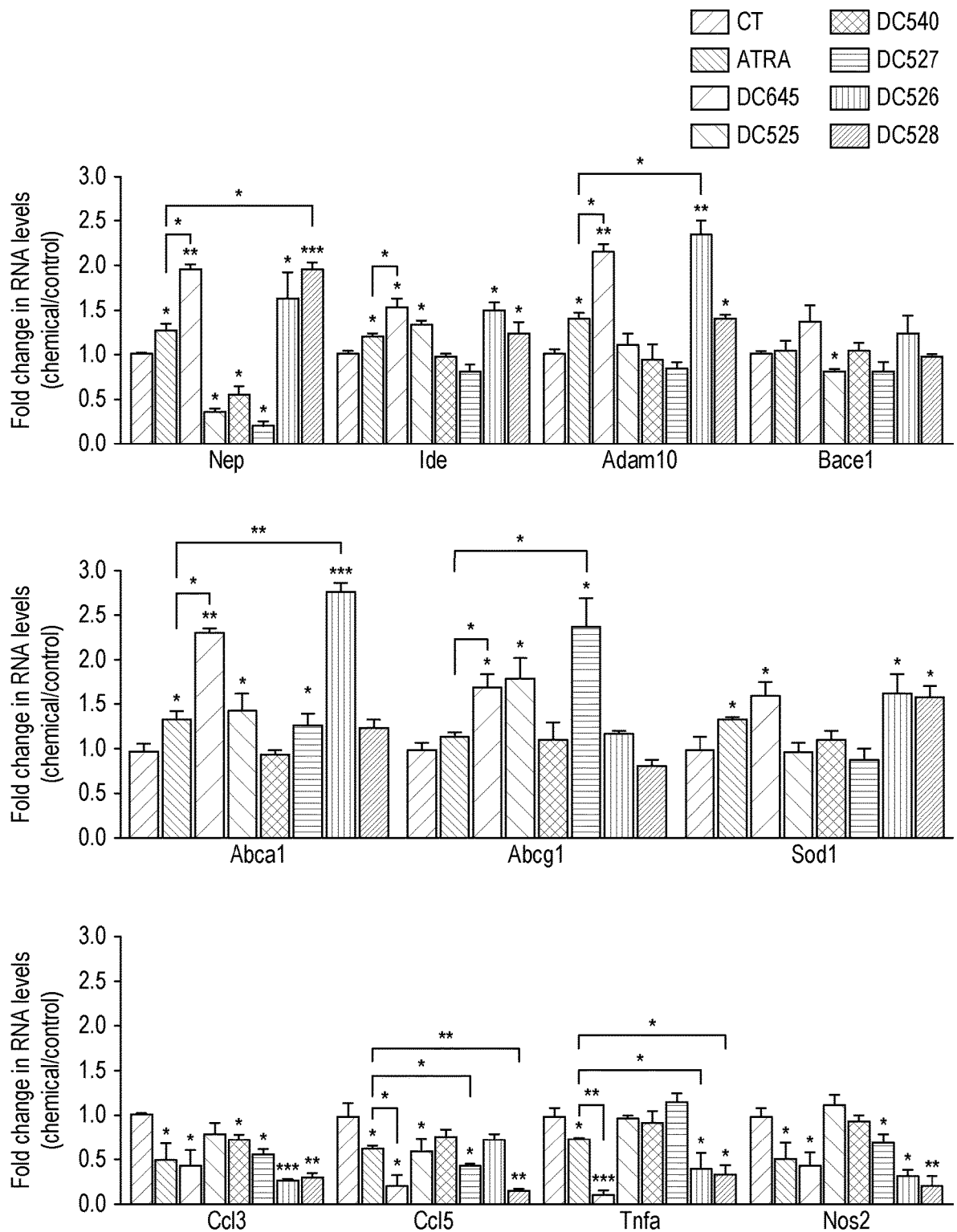
FIG. 7 shows data relating to the transcriptional regulation of Alzheimer's disease-related genes in rat mixed primary neuronal/glial cultures following treatment with retinoids.

The data shown in FIG. 7 demonstrates that DC645, DC528 and DC526 downregulated inflammation genes (Ccl5, TNFα and Nos2) and upregulated neuroprotection (Abca1, Abcg1, Igf1 and Igf2) and non-amyloidogenic pathway genes (Nep, Ide and Adam10) taking amyloid precursor down the pathway that does not generate toxic amyloid fragments.

EXAMPLE 3: MDCK-MDR1 PERMEABILITY ASSAY

This assay is used to measure the permeability of test compound in the apical to basolateral (A-B) and basolateral to apical (B-A) direction across MDCK-MDR1 cells and to determine the efflux ratio (ER), which shows whether the compound undergoes active efflux. Thus, this assay is a valuable in vitro surrogate for blood-brain permeability and CNS exposure

3.1 Experimental Procedure

MDCK-MDR1 cells obtained from the NIH (Rockville, MD, USA) are used between passage numbers 6-30. Cells are seeded onto Millipore Multiscreen Transwell plates at $3.4\times10^5$ cells/cm$^2$. The cells are cultured in DMEM and media is changed on day 3. On day 4 the permeability study is performed. Cell culture and assay incubations are carried out at 37° C. in an atmosphere of 5% $CO_2$ with a relative humidity of 95%. On the day of the assay, the monolayers are prepared by rinsing both apical and basolateral surfaces twice with Hanks Balanced Salt Solution (HBSS) at the desired pH warmed to 37° C. Cells are then incubated with HBSS at the desired pH in both apical and basolateral compartments for 40 min to stabilise physiological parameters. The dosing solutions are prepared by diluting test compound with assay buffer to give a final test compound concentration of 10 μM. Analytical standards are prepared from test compound DMSO dilutions and transferred to buffer, maintaining a 1% v/v DMSO concentration; buffer is composed of supplemented HBSS pH 7.4. For assessment of A-B permeability, HBSS is removed from the apical compartment and replaced with test compound dosing solution. The apical compartment insert is then placed into a companion plate containing fresh buffer (containing 1% v/v DMSO). For assessment of B-A permeability, HBSS is removed from the companion plate and replaced with test compound dosing solution. Fresh buffer (containing 1% v/v DMSO) is added to the apical compartment insert, which is then placed into the companion plate. At 60 min the apical compartment inserts and the companion plates are separated and apical and basolateral samples diluted for analysis. Test compound permeability is assessed in duplicate. Compounds of known permeability characteristics are run as controls on each assay plate. Test and control compounds are quantified by LC-MS/MS cassette analysis using a 7-point calibration with appropriate dilution of the samples. The starting concentration ($C_0$) is determined from the dosing solution and the experimental recovery calculated from $C_0$ and both apical and basolateral compartment concentrations.

3.2 Data Analysis

The permeability coefficient ($P_{app}$) for each compound is calculated from the following equation:

$$P_{app} = \left(\frac{dQ/dt}{C_0 \times A}\right)$$

Where dQ/dt is the rate of permeation of the drug across the cells, $C_0$ is the donor compartment concentration at time zero and A is the area of the cell monolayer. $C_0$ is obtained from analysis of the dosing solution. An efflux ratio (ER) is calculated from mean A-B and B-A data. This is derived from:

$$ER = \frac{P_{app(B-A)}}{P_{app(A-B)}}$$

3.3. Biological Study

The membrane permeability of a number of compounds of Formula I were measured in the MDCK-MDR1 assay described previously. The permeability ($P_{app}$, nm/s) and efflux ratio (ER) for compounds was determined and compared with those for the closely-related reference compound EC23. The results are summarised in Table 2:

TABLE 2

Permeability and efflux ratio of compounds of formula I, versus reference compound EC23.

| Compound/Structure | | Papp (nm/s) | ER |
|---|---|---|---|
| EC23 | (structure) | 0 | — |
| DC526 | (structure) | 0 | — |
| DC528 | (structure) | 0 | — |
| DC645 | (structure) | 349 | 0.6 |

The results shown in Table 2 demonstrate that some compounds of Formula (I) can show considerable improvements in permeability and lack of efflux in the MDCK-MDR1 assay and, thus, can be expected to show considerable improvements in blood brain barrier penetration and CNS exposure. As treatment of CNS disorders, including ALS and Alzheimer's disease, requires exposure of CNS targets to sufficiently-high concentrations of therapeutic agent, it is clear that optimal CNS exposure is an essential characteristic in a drug for the treatment of these disorders. Thus, investigated compounds of Formula (I) show significantly improved drug-like characteristics compared to the literature compound EC23. This improvement in CNS exposure represents a surprising and unexpected discovery.

EXAMPLE 4: TURBIDIMETRIC AQUEOUS SOLUBILITY

Example 4.1 Experimental Procedure

Test compound (10 mM in DMSO) is serially diluted to give solutions of 0.1, 0.3, 1 and 3 mM in DMSO. Each test compound concentration is then further diluted 1 in 100 in buffer (0.01 M phosphate buffered saline pH 7.4) so that the final DMSO concentration was 1% and the final test compound concentrations were 1, 3, 10, 30 and 100 μM. The experiment was performed at 37° C. and each concentration sample was incubated in 7 replicate wells. The plates were incubated for 2 hr at 37° C. before the absorbance was measured at 620 nm. The solubility of the sample was estimated from the concentration of test compound that produced an increase in absorbance above vehicle control (i.e., 1% DMSO in buffer).

4.2 Biological Study

The solubility of a number of compounds of the Formula (I) were measured in the turbidimetric aqueous solubility assay described previously. The solubility for compounds was determined and compared with those for the closely-related reference compound EC23. The results are summarised in Table 3:

TABLE 3

Solubility of compounds of formula I, versus reference compound EC23.

| Compound | Structure | μM |
|---|---|---|
| EC23 | (structure) | 6.5 |
| DC526 | (structure) | 20 |
| DC528 | (structure) | 20 |
| DC645 | (structure) | >100 |

The results shown in the above table demonstrate that compounds of Formula I can show considerable improvements in solubility and, thus, can also be expected to show considerable improvements in a number of biological properties, including absorption and target exposure. Again, this represents a surprising and unexpected discovery.

It will be understood that where, throughout the description, compounds are described for use in the treatment of a condition or disease which is alleviated by the activation of retinoic acid receptors (RAR), that this represents a disclosure of these compounds per se.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope of the present disclosure. Accordingly, the various embodiments disclosed herein are not intended to be limiting, with the true scope being defined by the following claims.

The invention claimed is:

1. A compound of formula I:

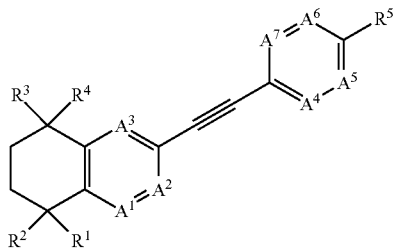

in which:
A$^1$ is N or CR$^6$;
A$^2$ is N or CR$^7$;
A$^3$ is N or CR$^8$;
R$^6$ and R$^8$, are each independently hydrogen, C$_1$-C$_{10}$ alkyl, F, Br or Cl;
R$^9$ is independently hydrogen, C$_1$-C$_{10}$ alkyl, F, Br, Cl or —OCR$^9$ in which R$^9$ is H or C$_3$-C$_6$ alkyl;
R$^1$ to R$^4$ are each independently C$_1$-C$_{10}$ alkyl, or R$^1$ and R$^2$ and/or R$^3$ and R$^4$ join to form a 3-membered ring;
A$^3$ is N or CR$^{12}$;
A$^5$ is N or CR$^{13}$;
A$^6$ is N or CR$^{14}$;
A$^7$ is N or CR$^{15}$;
each R$^{13}$ to R$^{15}$ is independently H, halogen or haloalkyl C$_1$-C$_{10}$, and
R$^5$ is —C(=O)R$^{16}$ or —C(=O)OR$^{16}$ in which R$^{16}$ is H or C$_{1-10}$ alkyl;
with the proviso that at least one of A$^1$ to A$^3$ is N;
in free or in salt form.

2. The compound as claimed in claim 1, wherein A$^1$ and A$^3$ are N.

3. The compound as claimed in claim 1, wherein A$^2$ is CR$^7$.

4. The compound as claimed in claim 3, R$^7$ is hydrogen.

5. The compound as claimed in claim 1, wherein R$^5$ is —COOH.

6. The compound as claimed in claim 1, wherein at least one of A$^4$, A$^5$ or A$^6$ is CF.

7. The compound according to claim 1, wherein the compound is selected from the group consisting of:

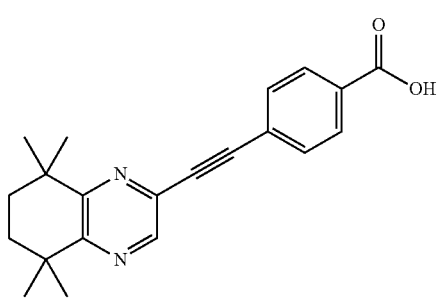

DC645

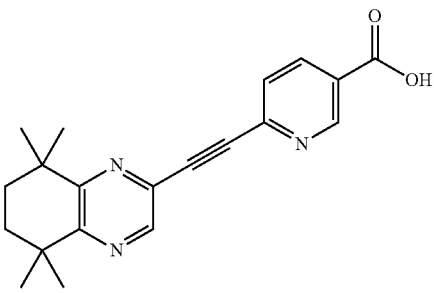

DC650

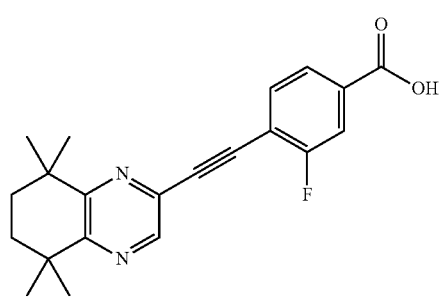

DC712

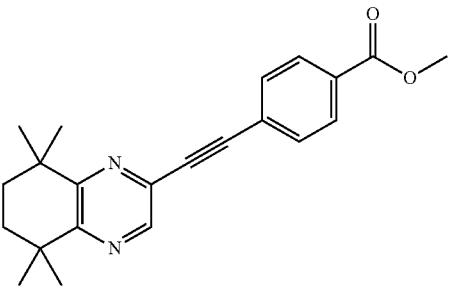

and

DC641

8. The compound according to claim 7, wherein the compound is

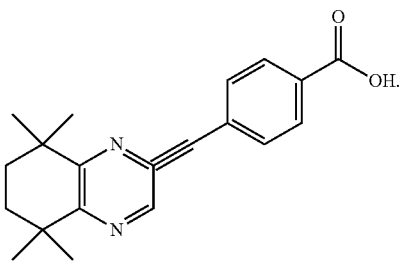

DC645

9. The compound of formula I as defined in claim 1, in a manufacture of a medicament for use in the treatment of a disease or condition which is alleviated by the activation of RAR.

10. A method of treatment of a patient with a disease or condition which is alleviated by the activation of RAR, the method comprising administering to a patient a therapeutically effective amount of the compound of formula I, wherein formula I is as defined in claim 1.

11. A pharmaceutical composition comprising the compound of formula I as defined in claim 1, optionally in conjunction with one or more pharmaceutically acceptable excipients, diluents or carriers, for use in the treatment of a disease or condition which is alleviated by the activation of RAR.

12. A method of screening the compounds as claimed in claim 1 for therapeutic potential in the treatment of conditions or diseases which are alleviated by the activation of RAR, the method comprising:
   performing an assay to determine the efficacy ($E_{max}$) of the compound in activating a RAR as an indicator of genomic activity;
   performing an assay to determine the efficacy ($E_{max}$) of the compound as an indicator of non-genomic activity;
   for each assay, comparing the $E_{max}$ to a baseline value; and
   selecting the compounds which has an $E_{max}$ above the baseline value in both assays for further investigation.

13. The method as claimed in claim 12, wherein the assay to determine the efficacy ($E_{max}$) of the compound as an indicator of non-genomic activity is a kinase phosphorylation assay.

14. The method as claimed in claim 13, wherein the kinase phosphorylation assay is an ERK1/2 phosphorylation assay.

\* \* \* \* \*